(12) United States Patent
Moore et al.

(10) Patent No.: US 9,679,110 B2
(45) Date of Patent: Jun. 13, 2017

(54) DEVELOPING PREDICTIVE DOSE-VOLUME RELATIONSHIPS FOR A RADIOTHERAPY TREATMENT

(75) Inventors: Kevin L. Moore, St. Louis, MO (US); Sasa Mutic, St. Louis, MO (US); Ryan Scott Brame, St. Louis, MO (US); Lindsey Appenzoller, St. Louis, MO (US)

(73) Assignee: Washington University, St. Louis, MO (US)

( * ) Notice: Subject to any disclaimer, the term of this patent is extended or adjusted under 35 U.S.C. 154(b) by 872 days.

(21) Appl. No.: 13/486,809

(22) Filed: Jun. 1, 2012

(65) Prior Publication Data
US 2012/0310615 A1    Dec. 6, 2012

Related U.S. Application Data

(60) Provisional application No. 61/493,415, filed on Jun. 3, 2011.

(51) Int. Cl.
| | |
|---|---|
| *G01N 33/48* | (2006.01) |
| *G01N 33/50* | (2006.01) |
| *G06F 19/00* | (2011.01) |
| *A61N 5/10* | (2006.01) |
| *G06F 19/24* | (2011.01) |

(52) U.S. Cl.
CPC ....... *G06F 19/3437* (2013.01); *A61N 5/1031* (2013.01); *G06F 19/3481* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 7,283,610 B2* | 10/2007 | Low et al. | 378/65 |
| 2004/0228435 A1* | 11/2004 | Russell | 378/18 |
| 2007/0276777 A1* | 11/2007 | Krishnan | A61N 5/103 |
| | | | 706/46 |

OTHER PUBLICATIONS

Low et al. Quantitative dosimetric verification of an IMRT planning and delivery system. Radiotherapy and Oncology, vol. 49, 1998, pp. 205-216.*
Low et al. Evaluation of polymer gels and MRI as a 3-D dosimeter for intensity-modulated radiation therapy. Medical Physics, vol. 26, 1999, pp. 1542-1551.*
Moore et al., "Experience-based Quality Control of Clinical IMRT Planning" Int. J Radiat Oncol Biol Phys, 2011, vol. 81, No. 2, pp. 545-551.
Wu et al., "Patient geometry-driven information retrieval for IMRT treatment plan quality control", Med Phys, 2009, vol. 36, pp. 5497-5505.

* cited by examiner

*Primary Examiner* — Russell S Negin
(74) *Attorney, Agent, or Firm* — Armstrong Teasdale LLP

(57) ABSTRACT

Embodiments develop a predictive dose-volume relationships for a radiation therapy treatment is provided. A system includes a memory area for storing data corresponding to a plurality of patients, wherein the data comprises a three-dimensional representation of the planning target volume and one or more organs-at-risk. The data further comprises an amount of radiation delivered to the planning target volume and the one or more organs-at-risk. The system further includes one or more processors programmed to access, from the memory area, the data and to develop a model that predicts dose-volume relationships using the three-dimensional representations of the planning target volume and the one or more organs-at-risk. The model is being derived from correlations between dose-volume relationships and calculated minimum distance vectors between discrete volume elements of the one or more organs-at-risk and a boundary surface of the planning target volume.

18 Claims, 44 Drawing Sheets

DEVELOPING PREDICTIVE DOSE-VOLUME RELATIONSHIPS FOR A RADIOTHERAPY TREATMENT

CROSS REFERENCE TO RELATED APPLICATION

This application claims priority to U.S. provisional patent application No. 61/493,415 filed Jun. 3, 2011, which is incorporated herein in its entirety.

BACKGROUND

Conventional radiation therapy techniques include the use of Intensity Modulated Radiation Therapy ("IMRT"), Arc Therapy, Three-Dimensional Conformal Radiation Therapy ("3-D CRT"), Particle Therapy, or Brachytherapy. The use of IMRT, for example, allows a radiation oncologist to treat a patient from multiple angles while varying the shape and dose of a radiation beam and thereby providing greatly enhanced ability to deliver radiation to a region of interest while avoiding excess irradiation of nearby healthy tissue.

Various treatment planning optimization techniques exist for developing radiation fluence patterns for external beam radiation therapy treatment plans. Treatment planning starts typically with images of an area of interest (e.g., slices from a CT scan), a desired dose of radiation which is to be delivered to a region of interest, such as a tumor, and "organs-at-risk" (OAR), which represent healthy tissues that are adjacent to or near the area of interest. A portion of a patient's anatomy that is intended to receive a therapeutic prescribed dose is referred to as a "planning target volume" (PTV). Both the PTV and any OAR may have complex three-dimensional shapes adding to the difficulty of preparing a treatment plan.

A variety of algorithms have been developed to solve an "inverse problem" of devising and optimizing a three-dimensional treatment plan for irradiating a planning target volume from a variety of angles to deliver a desired radiation dose to a region of interest while minimizing irradiation of nearby tissue (e.g., an OAR). Conventional treatment planning software packages are designed to import 3-D images from a diagnostic imaging source, for example, x-ray computed tomography (CT) scans. CT is able to provide an accurate three-dimensional model of a volume of interest (e.g., tumor bearing portion of the body) generated from a collection of CT slices and, thereby, the volume requiring treatment can be visualized in three dimensions.

During radiotherapy planning, volumetric structures are delineated to be targeted or avoided with respect to the administered radiation dose. That is, the radiation source is positioned in a sequence calculated to deliver the radiation dose that as closely as possible conforms to the tumor requiring treatment, while avoiding exposure of nearby healthy tissue (e.g., OAR). Once the region of interest (e.g., tumor) has been defined, and the critical normally-functioning tissue volumes have been specified, the responsible radiation oncologist specifies a desired radiation dose to the PTV and the allowable dose to OARs. Guided by a treatment planner or medical physicist, the software then produces a treatment plan that attempts to meet clinical dosimetric objectives expressed in terms of "dose-volume relationships." These dose-volume relationships range from simple single-valued metrics (e.g. mean dose) to the three-dimensional dose matrix itself. One commonly used embodiment of a dose-volume relationship is the dose-volume histogram (DVH) that summarizes the frequency distribution of radiation doses in a particular volumetric structure (PTV or OAR).

However, the above methods allow a planner to change objective criteria and guide inverse planning algorithms to a case-by-case solution, which then undergoes clinical review by a radiation oncologist before a patient is treated. Thus, the evaluation criteria are very subjective and depend on a planner's level of experience and an amount of time the planner has in developing the plan. In addition, planners and reviewers often accept plans when further sparing of an OAR is possible.

SUMMARY

In one aspect, a system for developing a predictive dose-volume relationship for an intensity modulated radiation therapy treatment is provided. The system includes a memory area for storing data corresponding to a plurality of patients, wherein the data comprises a three-dimensional representation of the planning target volume and one or more organs-at-risk. The data further comprises an amount of radiation delivered to the planning target volume and the one or more organs-at-risk. The system further includes one or more processors programmed to access, from the memory area, the data corresponding to the plurality of patients, the data comprising a three-dimensional representation of the planning target volume and one or more organs-at-risk, and the data comprising an amount of radiation delivered to the planning target volume and the one or more organs-at-risk. The processor is also programmed to develop a model that predicts dose-volume relationships using the three-dimensional representations of the planning target volume and the one or more organs-at-risk. The model is being derived from correlations between dose-volume relationships and calculated minimum distance vectors between discrete volume elements of the one or more organs-at-risk and a boundary surface of the planning target volume. Alternatively, there could may other suitable methods to derive the model.

In another aspect, a method is provided. The method includes receiving data corresponding to a radiation of a planning target volume in a plurality of patients, wherein the data comprises a three-dimensional representation of the planning target volume and one or more organs-at-risk. The data further comprises an amount of radiation delivered to the planning target volume and the one or more organs-at-risk, and based on the received data. The method also includes determining a predictive dose-volume relationship for irradiating the planning target volume while sparing organs-at-risk.

In yet another aspect, one or more storage media embodying computer-executable components are provided. The components include an interface component that when executed by at least one processor causes the at least one processor to receive data corresponding to a radiation of a planning target volume in a plurality of patients. The data comprises a three-dimensional representation of the planning target volume and one or more organs-at-risk. The data further comprises an amount of radiation delivered to the planning target volume and the one or more organs-at-risk. The components also include a correlation component that when executed by the at least one processor causes the at least one processor to determine predictive dose-volume relationships for sparing organs-at-risk while irradiating the planning target volume based on the received data.

BRIEF DESCRIPTION OF THE DRAWINGS

Corresponding reference characters indicate corresponding parts throughout the drawings bound.

DETAILED DESCRIPTION

One feature of an effective radiation treatment system is homogeneity of dose delivered to the intended target of the therapeutic radiation. Homogeneity is the uniformity of a radiation dose over a volume of a planning target volume (e.g., pathological anatomy such as a tumor, lesion, vascular malformation, and the like).

Another feature of an effective radiation treatment is the sparing, to the highest degree possible, of the normally-functioning tissue surrounding the PTV from the ancillary radiation needed to deliver the therapeutic dose to the PTV. This can be expressed in many ways that describe the distribution of radiation across an organ-at-risk, relating the dose to the volumetric representation of the OAR. One such expression of a dose-volume relationship is the dose-volume histogram, i.e. a summary of the distribution of radiation deposition in a particular structure (PTV or OAR).

A variety of algorithms have been developed to solve an "inverse problem" of devising and optimizing a three-dimensional treatment plan to deliver a desired radiation dose to an area of interest while minimizing irradiation of nearby tissue. Currently, however, planners manually tweak planning elements (e.g., inverse planning optimization parameters) to optimize a treatment plan until it is deemed to be clinically acceptable. As such, Intensity Modulated Radiation Therapy ("IMRT") planning can be both subjective and time-consuming process of trial-and-error. Even if the human elements of this problem are eliminated through planning automation, quality control methods would be required to verify that the product of such automation has been properly implemented with respect to past experience.

The present disclosure provides a system and method for developing a predictive dose-volume relationship (in this embodiment, a dose-volume histogram) for a radiation therapy treatment based on geometric measurements, such as boundary distance vectors. The system and method correlates the three-dimensional representation of the PTV and the one or more OAR, represented in this embodiment by a calculated set of minimum magnitude distance vectors between organ voxels and the boundary surface of the planning target volume (hereby referred to as "boundary distance vectors"). The predictive dose-volume relationship is based on data from a prior training set of patients, whereby the system and method establishes a functional relationship between boundary distance vectors and a probability distribution of radiation dose for an organ voxel at that position.

Figure 1:
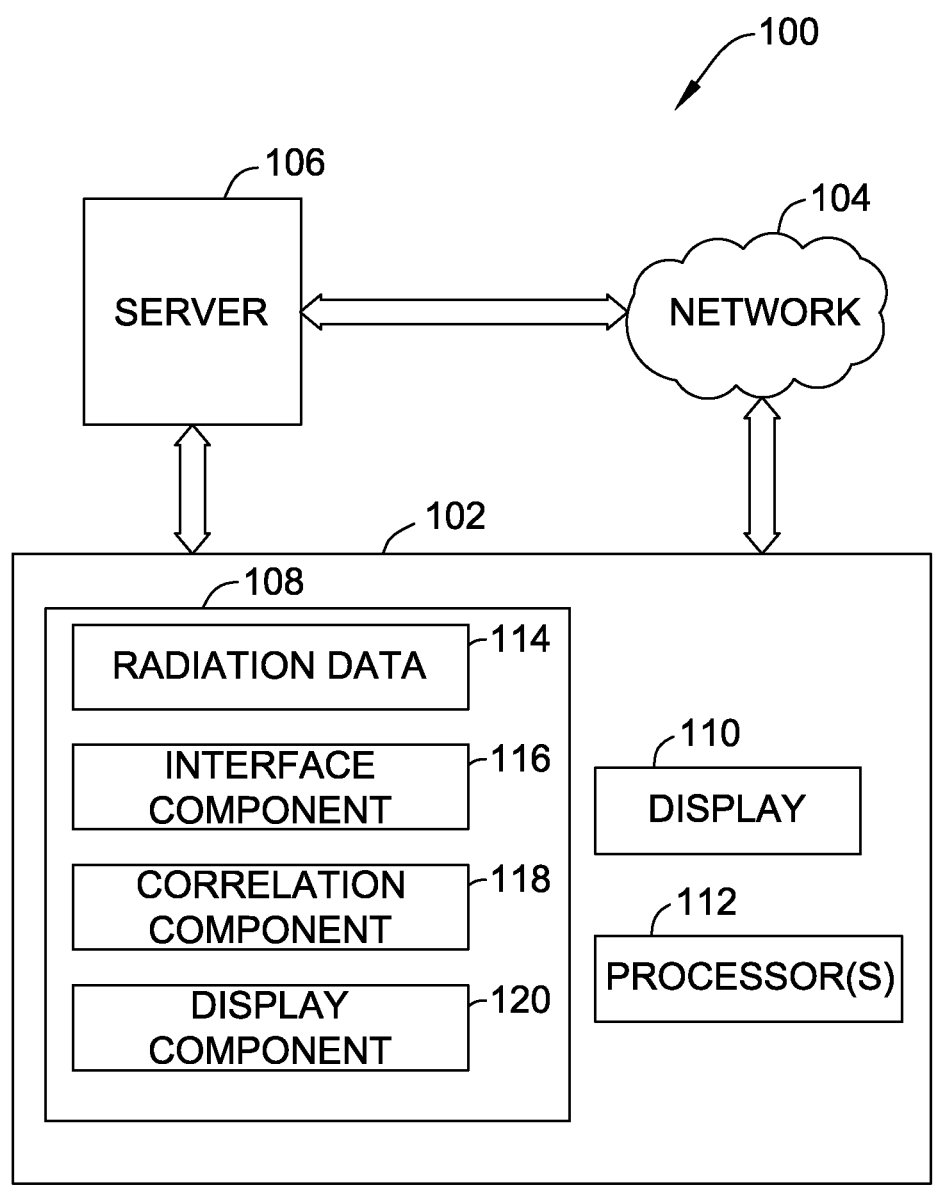
FIG. 1 is an exemplary block diagram of a system for developing a predictive dose-volume relationship for an IMRT treatment.

Referring now to FIG. 1, an exemplary block diagram of a system 100 is provided. System 100 is but one example of a suitable system and is not intended to suggest any limitation as to the scope of use or functionality of the present disclosure. Further, system 100 should not be interpreted as having any dependency or requirement relating to any one or combination of components illustrated herein.

System 100 includes a computing device 102, a network 104, and a server 106. While some embodiments of the disclosure are illustrated and described herein with reference to the server 106 being a server computing device, aspects of the disclosure are operable with any device that performs the functionality illustrated and described herein, or its equivalent, such as in peer-to-peer systems. For example, embodiments of the disclosure are operable with netbooks, desktop computing devices, laptop computers, and other computing devices. In such embodiments, data may be stored by a cloud service and accessible by any computing device implementing functionality of the disclosure.

Referring again to FIG. 1, an exemplary block diagram illustrates the computing device 102 having a memory area 108 for storing components for developing a predictive dose-volume relationship for a radiotherapy treatment. Computing device 108 further includes a display 110 and at least one processor 112. Display 110 may be, for example, a capacitive touch screen display that is integrated into computing device 102 or external to computing device 102. User input functionality is provided in display 110 which acts as a user input selection device as well as a means to provide a user with a predictive dose-volume relationship. In embodiments, display 110 is configured to be responsive to a user pressing contact on display 110 to selectively perform functionality. Thus, a user can operate the desired troubleshooting functions available with computing device 102 by contacting a surface of display 110 as well as other functions provided herein.

Memory area 108 stores radiation data 114 corresponding to an irradiation of a PTV (not shown) in a plurality of patients. Radiation data 114 includes a three-dimensional representation of a PTV and one or more OAR (not shown) for each patient's treatment. Radiation data 114 further includes an amount of radiation delivered to the PTV and any OAR as well as one or more computer-executable components. Exemplary components include, but are not limited to, an interface component 116, a correlation component 118, and a display component 120. While radiation data 114 and components 116-120 are shown to be stored in memory area 108, radiation data 114 and components 116-120 may be stored and executed from a memory area remote from computing device 102. For example, radiation data 114 may be stored in a cloud service, a database, or other memory area accessible by computing device 102. Such embodiments reduce the computational and storage burden on computing device 102.

Processor 112 executes computer-executable instructions for implementing aspects of the disclosure. In some embodiments, processor 112 is transformed into a special purpose microprocessor by executing computer-executable instructions or by otherwise being programmed. For example, processor 112 may execute interface component 116 and correlation component 118.

Interface component 116, when executed by the processor 112, causes the processor 112 to access, from memory area 108, radiation data 114 corresponding to a radiation of a planning target volume in a plurality of patients. In one embodiment, radiation data 114 includes a three-dimensional representation of the PTV and one or more OAR for a treatment corresponding to each of the plurality of patients. Radiation data 114 further includes an amount of radiation delivered to the PTV and the one or more OAR for a treatment corresponding to each of the plurality of patients. Correlation component 118, when executed by the processor 112, causes the processor 112 to determine predictive dose-volume relationships for the PTV and the one or more OAR.

In general, processor 112 may be programmed with instructions such as described herein with reference to the components illustrated in FIG. 1, and the operations illustrated and next described in FIG. 3.

Figure 2:
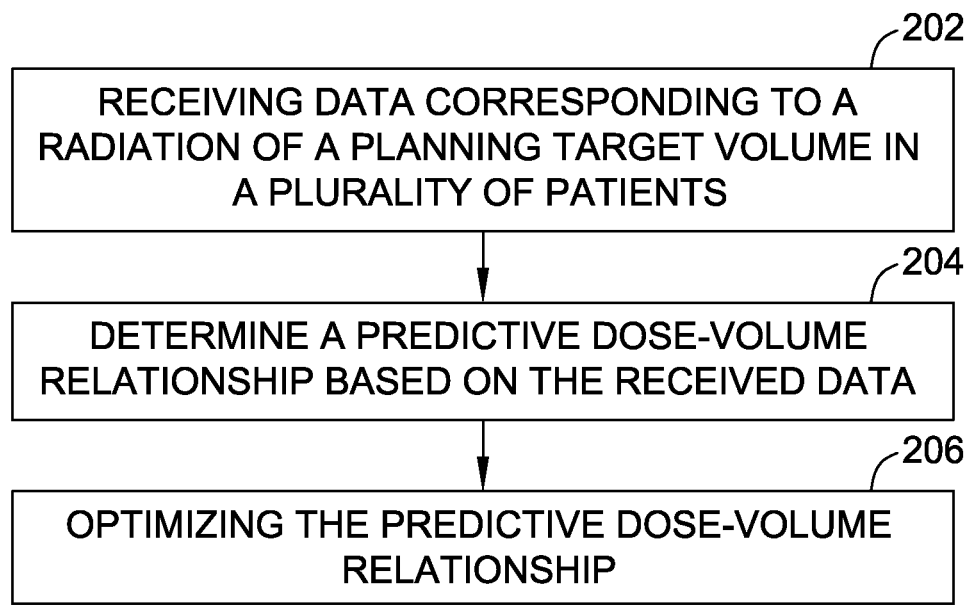
FIG. 2 is an exemplary flow chart illustrating a process for developing predictive dose-volume relationships for a radiation therapy treatment and applying that model to predict the dose-volume relationships in a new patient.

Referring next to FIG. 2, an exemplary flow chart illustrates a process for developing a predictive dose-volume relationship for a radiotherapy treatment. At 202, radiation data corresponding to a radiation of a PTV in a plurality of patients is received. The radiation data includes a three-dimensional representation of the PTV and one or more OAR, as well as an amount of radiation delivered to the PTV and the one or more OAR. Based on a model that is developed through an analysis of prior treatment plans, and in particular, using geometric measurements (e.g., boundary distance vectors) from the radiation data as the determining dosimetric feature, a dose-volume relationship (e.g., a DVH) of a radiotherapy plan can be predicted.

At 204, a predictive dose-volume relationship is determined based on the received data. In one embodiment, the predictive dose-volume relationship is determined by first calculating a dose-volume relationship corresponding to the irradiation of the PTV for each patient, and thereafter determining a correlation between the calculated DVHs and the set of boundary distances from the one or more OAR to the PTV. At 206, the predictive dose-volume relationship is optimized. In one embodiment, optimizing the predictive dose-volume relationship includes comparing the predictive dose-volume relationship to each of the calculated dose-volume relationships and determining which of the calculated dose-volume relationships are optimal based on the comparing. In one embodiment, once the optimal dose-volume relationships are determined, a model embodying the correlation between the optimal dose-volume relationships and the boundary distance vectors from the one or more OAR to the PTV is determined. To employ the resultant model, data corresponding to the three-dimensional representation of the PTV and the one or more OAR of a new patient is received. The data is input to the model and the predicted dose-volume relationships for the PTV and the one or more OAR are calculated and presented.

Exemplary Operating Environment

A computer or computing device such as computing device 102 and server 106 described herein have one or more processors or processing units, system memory, and some form of computer readable media. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. Communication media typically embody computer readable instructions, data structures, program modules, or other data in a modulated data signal such as a carrier wave or other transport mechanism and include any information delivery media. Combinations of any of the above are also included within the scope of computer readable media.

The computer may operate in a networked environment using logical connections to one or more remote computers, such as a remote computer. Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well known computing systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

Aspects of the invention transform a general-purpose computer into a special-purpose computing device when configured to execute the instructions described herein.

The embodiments of the system and method for developing a predictive dose-volume relationship for an intensity modulated radiation therapy treatment, as described herein, were used in the following exemplary experiment.

EXPERIMENT

In this experiment, which represents one possible embodiment of this disclosure, a framework to predict achievable OAR DVHs was derived based on a correlation of expected dose to the distance from a voxel to the PTV surface (r). OAR voxels sharing a range of r were computed as sub-volumes. A three-parameter, skew-normal probability distribution was used to fit sub-volume dose distributions, and DVH prediction models were developed by fitting the evolution of the skew-normal parameters as a function of r with generalized polynomials. A cohort of 20 prostate and 24 head-and-neck IMRT plans with identical clinical objectives were used to train organ-specific AVERAGE models for rectum, bladder, and parotid glands. A sum of residuals analysis quantifying the integrated difference between DVHs was utilized to score the concordance of one DVH to another. The AVERAGE model's predictive ability was evaluated by application of the model to an independent validation cohort of 20 prostate IMRT plans (i.e. "new" patients as yet unseen by the model). Statistical comparison of the residual sums between the training and validation cohort quantified the accuracy of the AVERAGE model. Restricted sums of residuals that ignore regions where the clinical DVH is better use the predicted DVH to identify potentially sub-optimal plans, wherein sub-optimality is defined to be a case where the clinical OAR DVH was in demonstrable excess of a model's prediction. A REFINED model for each organ was obtained by excluding cases from the training cohort with restricted residual sums. The REFINED model was then re-applied to the entire training cohort with the restricted sum of residuals for this cohort representing the best estimate of the potential case-by-case improvement. All training cases were re-planned and re-evaluated by the attending physician that approved the original clinical plan to ensure clinical acceptability of the new solutions. The residual sum between the original and re-planned DVHs represented the realized gains under re-planning, quantifying the accuracy of the REFINED model's outlier identification.

As described in more detail below, the results of this study demonstrate the ability to predict achievable OAR DVHs based on individual patient anatomy. The models were further capable of identifying sub-optimal plans that were subsequently brought within expected values via further optimization. This technique requires no manual intervention except for the appropriate selection of previous treatment plans with identical clinical quality evaluation criteria.

To understand the process of making prospective dosimetric predictions, the clinical goals of the IMRT planning process should be considered. For example, as shown below, Table 1 enumerates exemplary planning goals for prostate and head-and-neck. All treatment plans considered in this study attempted to meet these common goals, though the degree to which any individual plan optimally satisfied the multi-objective list was variable and previously unquantified.

This first goal of this experiment is to derive the mathematical learning framework necessary to, given a sufficient training set of clinical data, predict the expected OAR dose-volume histogram (DVH) for future cases based only on organ geometry. An automated framework for detection and rejection of sub-optimal plans from the training cohort is the second goal. Finally, this experiment seeks to provide a methodology for validating the two primary functions of predictive DVHs: (1) accurate dosimetric forecasting and (b) sensitive and specific detection of sub-optimal plans.

TABLE 1

Exemplary IMRT planning goals for prostate and head-and-neck treatments.

| Site | PTV/OAR | Objectives | |
|------|---------|------------|---|
| | | In-tact Prostate | |
| Prostate | PTV | 98% of PTV receives 100% of Rx; Maximum dose <107% of Rx | |
| | Rectum | V65 < 17%; V40 < 35%; Maxiumum dose as low as possible | |
| | Bladder | V65 < 25%; V40 < 50%; Maxiumum dose as low as possible | |
| | Femoral Heads | V50 < 10% of the total volume | |
| | Unspecified Tissue | Less than PTV dose; <5% exceeds PTV dose | |
| | | Bilateral Neck Treatment | Ipsliateral Neck Treatment |
| H&N | PTV | 95% of PTV >95% of Rx; Max dose <110% of Rx | 95% of PTV >95% of Rx; Max dose <110% of Rx |
| | Spinal Cord | Max dose 40 Gy | Max dose 40 Gy |
| | Spinal Cord + Margin | Max dose 52 Gy; <1% (or 1 cc) exceeds 50 Gy | Max dose 52 Gy; <1% (or 1 cc) exceeds 50 Gy |
| | Optic Nerves, Optic Chiasm | Max dose 54 Gy | Max dose 54 Gy |
| | Brainstem | Max dose 54 Gy; <1% exceeds 60 Gy | Max dose 54 Gy; <1% exceeds 60 Gy |

TABLE 1-continued

Exemplary IMRT planning goals for prostate and head-and-neck treatments.

| Site | PTV/OAR | Objectives | |
|---|---|---|---|
| | Brain | Max dose 60 Gy; <1% exceeds 65 Gy | Max dose 60 Gy; <1% exceeds 65 Gy |
| | Retina | Max dose 50 Gy; <5% exceeds 45 Gy | Max dose 50 Gy; <5% exceeds 45 Gy |
| | Larynx | As low as possible; mean Dose <45 Gy | As low as possible; mean Dose <25 Gy |
| | Upper Esophagus | As low as possible; mean Dose <45 Gy | As low as possible; mean Dose <25 Gy |
| | Parotid | Mean dose ≤26 Gy (at least one parotid) | Mean dose ≤10 Gy (contralateral parotid) |
| | Pharyngeal Constrictors | As low as possible; V60 < 60 Gy | As low as possible; V60 < 45 Gy |
| | Submandibular | Mean dose <39 Gy | Mean dose <24 Gy (contralateral) |
| | Oral Cavity | As low as possible; mean Dose Under 35 Gy | As low as possible; mean Dose <20 Gy |
| | Mandible | Max 70 Gy; <5% exceeds PTV Rx | Max 70 Gy; <5% exceeds PTV Rx |
| | Unspecified Tissue | Less than PTV Rx; <5% exceeds PTV Rx | Less than PTV Rx; <5% exceeds PTV Rx |

The starting assumption for this work involves the identification of a cohort of N site-similar IMRT plans that were developed using identical clinical goals and quality assessment criteria. The planning datasets are comprised of structure sets $SS_{ij}$ (i=1 . . . N cases, j=1 . . . M structures with j=I representing the PTV and j=2 . . . M representing M−1 OARs) and dose matrices $D_i = D_i(\vec{x})$, where $\vec{x}$ is the 3-D position vector with arbitrary origin. Operations on $SS_{ij}$ and $D_i$ result in differential DVH $$V_{ij}^r = \left(\frac{dV_j}{dD}\right)_i$$

for the $j^{th}$ OAR in the dataset, and summing $$V(SS_{ij}) = \sum_{D=0}^{\infty} \left(\frac{dV_j}{dD}\right)_i \cdot \Delta D$$

over a set of discreet dose bins ($\Delta D$) yields the OAR volume. The problems may be simplified by normalizing the dose matrices to the PTV prescription dose, i.e. $D_i \rightarrow \frac{D_i}{D_{Rx}}$, and employing normalized differential DVHs, i.e.

$$V'_{ij} \rightarrow \frac{V'_{ij}}{V(SS_{ij})}.$$

Finally, the familiar normalized cumulative DVH function $$DVH_{ij}(D) = 1 - \sum_{D}^{D} \left[\frac{V'_{ij}(\tilde{D})}{V(SS_{ij})}\right] \cdot \Delta D$$

was used for comparison between clinical DVHs and the predicted DVHs.

The boundary distance vector is given by Equation 1 below.

$$\vec{r}_i(\vec{x}) = \min\{\vec{x} - \vec{X}\} \forall \vec{X} \in SS_{ij} \quad (1)$$

In Equation 1, $\vec{r}_i(\vec{x})$ expresses the smallest magnitude vector that would translate a position vector $\vec{x}$ (in any coordinate system) to the boundary surface of the PTV (i.e., a position on the PTV boundary). While some features of IMRT dose distributions may in fact be correlated to the orientation components of the boundary distance vector, this experiment considers the magnitude as a spatial correlate, embodied in the boundary distance shown in Equation 2 below.

$$r_i(\vec{x}) = \|\vec{r}_i(\vec{x})\| \quad (2)$$

Figure 3A:
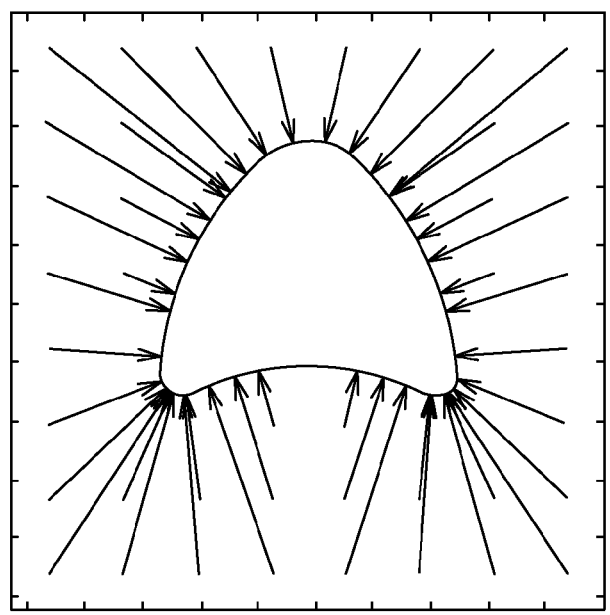
FIGS. 3A-3B depict the boundary distance vector and scalar fields.
Figure 3B:
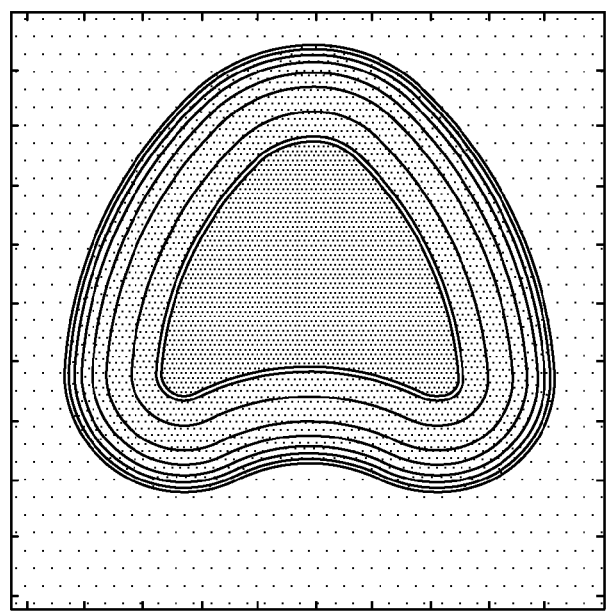

Equation 2 expresses the minimum distance between any point and the PTV surface boundary. Computing the boundary distance for a given instance is a purely geometric operation. FIG. 3A illustrates a vector field representation of $\vec{r}_i(\vec{x})$ around PTV contour $SS_{i1}$ (solid black) and FIG. 3B is an isodistance contour map representation of the scalar field $r_i(\vec{x})$. The connection between the boundary distance and an IMRT dose distribution is as yet undetermined, but the familiar notion of dose conformality is equivalent to a negative correlation between $D_i(\vec{x})$ and $r_i(\vec{x})$, at least at small boundary distances.

The structure sets $SS_{ij}$ can be recast as the locus of points that identify each anatomical construct. Should this data be expressed in terms of contours (sequence of closed loops) or masks (matrix of voxels with binary representation of occupied positions), $SS_{ij}$ identifies any position $\vec{x}$ as either inside or outside the $j^{th}$ structure of the $i^{th}$ dataset. This interpretation of $SS_{ij}$ combined with the definition of $r_i(\vec{x})$ yield the new object $A_{ijk}$, which is defined in Equation 3 below.

$$A_{ijk} = r_k \cap SS_{ij} \quad (3)$$

Figure 4:
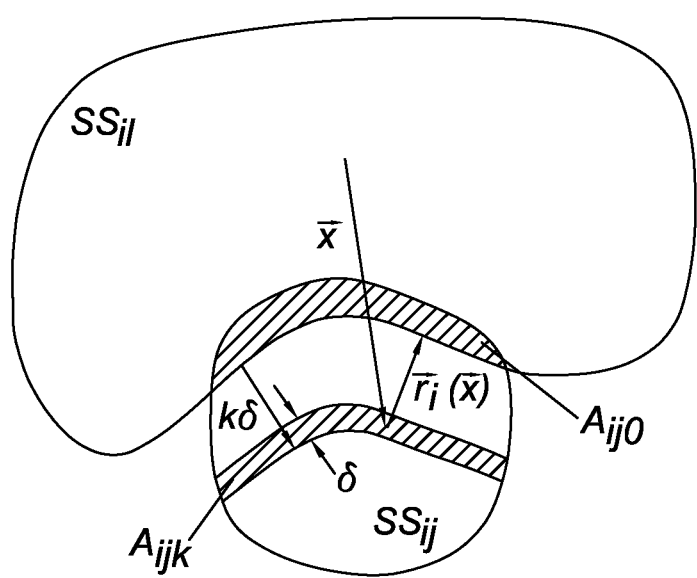
FIG. 4 is a schematic diagram of geometric constructs.

In Equation 3, $(k-1)\delta < r_k \leq k\delta$ with k=1 . . . ∞ and δ being a finite distance interval. Any overlap of the $j^{th}$ structure with the PTV is encompassed In $A_{ijk} \equiv SS_{i1} \cap SS_{ij}$. Thus, $A_{ijk}$ represents the locus of points inside the $j^{th}$ structure of the $i^{th}$ dataset that reside between a specified interval of distance from the PTV boundary, as shown in FIG. 4. More specifically, FIG. 4 is a diagrammatic representation of geometric constructs $r_i(\vec{x})$ and $A_{ijk}$.

$A_{ijk}$ is itself a structure and satisfies the geometric relationship $SS_{ij} = A_{ij0} \cup A_{ij1} \cup A_{ij2} \ldots \cup A_{ij\infty}$. Operations on $D_i$ and $A_{ijk}$ yield $\chi_{ijk}$, the differential DVH of $A_{ijk}.\chi_{ijk}$ can be considered a "sub-DVH" of the total organ DVH (as shown in FIGS. 5A and 5B), and as shown in Equation 4 below, $$V'_{ij} - \sum_{k=0}^{\infty} \chi_{ijk} \cdot V(A_{ijk}) \quad (4)$$

where $V(A_{ijk})$ is the volume of $A_{ijk}$. FIG. 5A is a graphical depiction of the $j^{th}$ OAR's differential DVH $V'_{ij}$ as summation over the $\chi_{ijk}$ sub-DVHs. FIG. 5B is more familiar cumulative DVH view of $$DVH_{ij}(D) = 1 - \sum_{\tilde{D}}^{D} \left[ \frac{V'_{ij}(\tilde{D})}{V(SS_{ij})} \right] \cdot \Delta D$$

for an OAR.

Figure 5A:
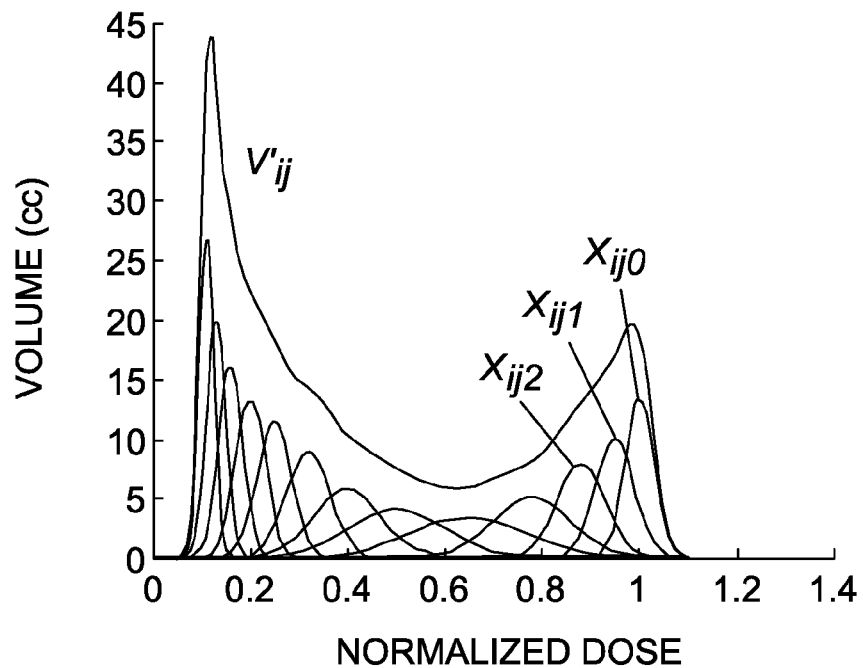
FIGS. 5A and 5B are graphs depicting associated differential and cumulative dose-volume histograms, respectively. The sub-DVHs Xijk represent the differential DVHs of the sub-volume elements Aijk depicted in FIG. 4.
Figure 5B:
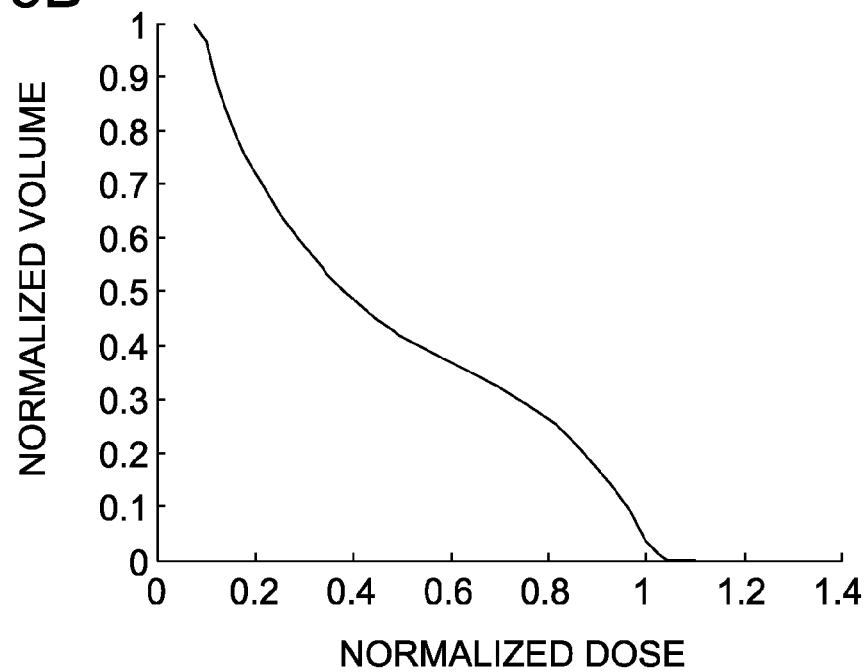
Figure 6A:
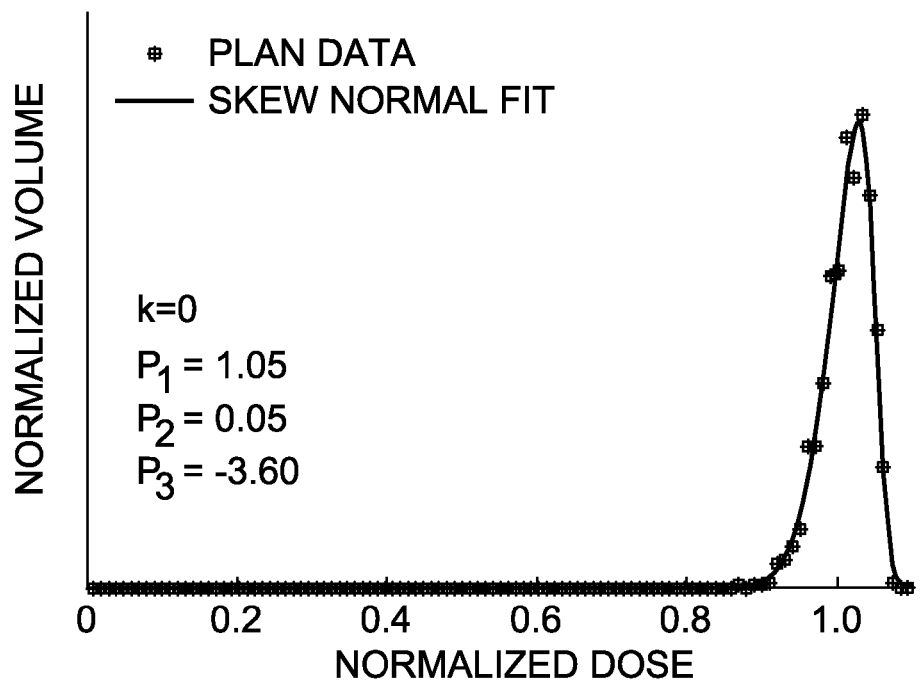
FIGS. 6A-6D are graphs depicting fits to rectum sub-volume DVHs with a generalized mathematical function.
Figure 6B:
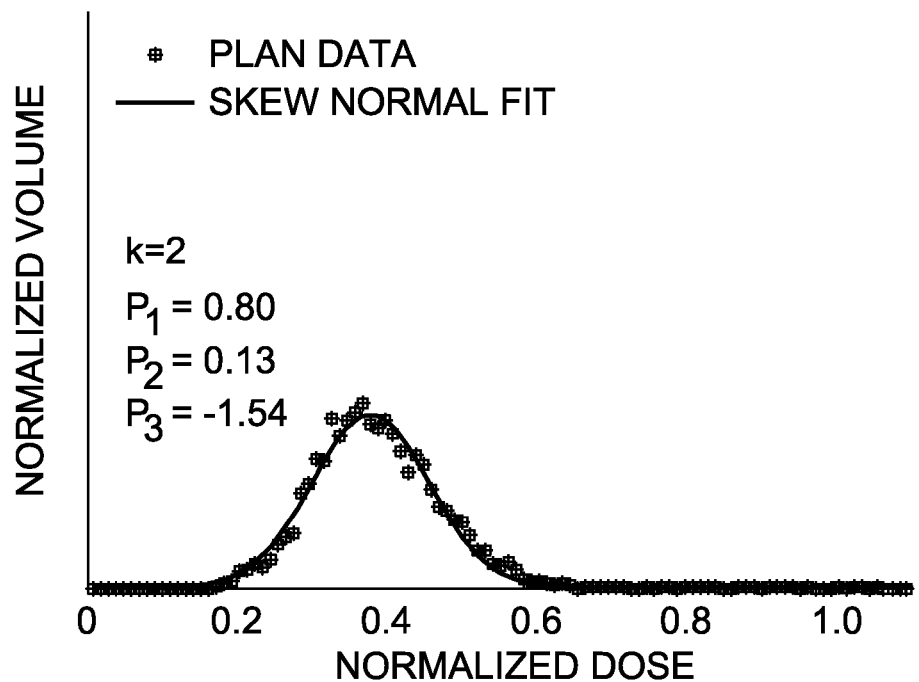
Figure 6C:
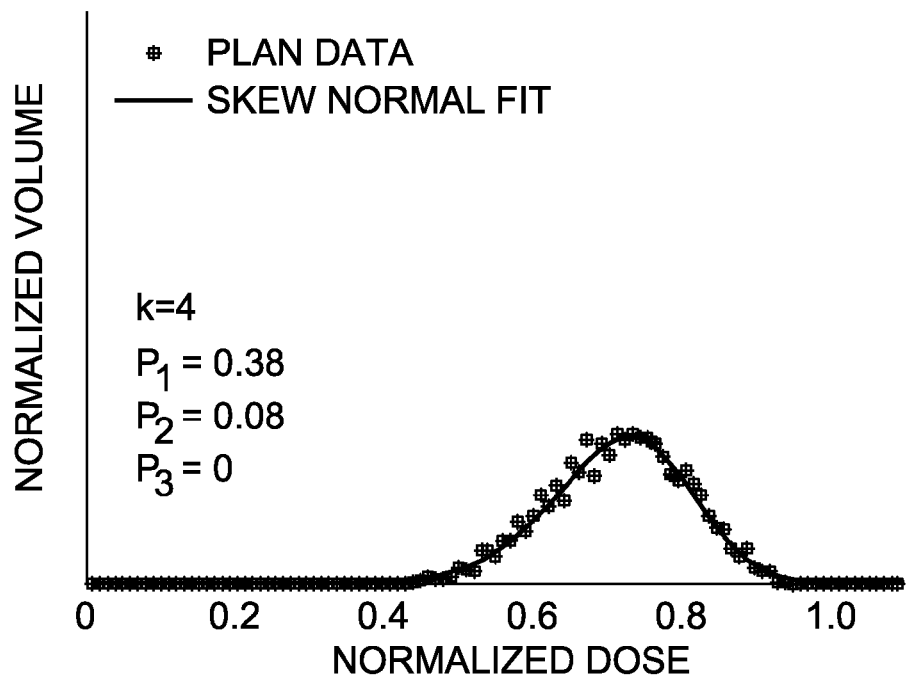
Figure 6D:
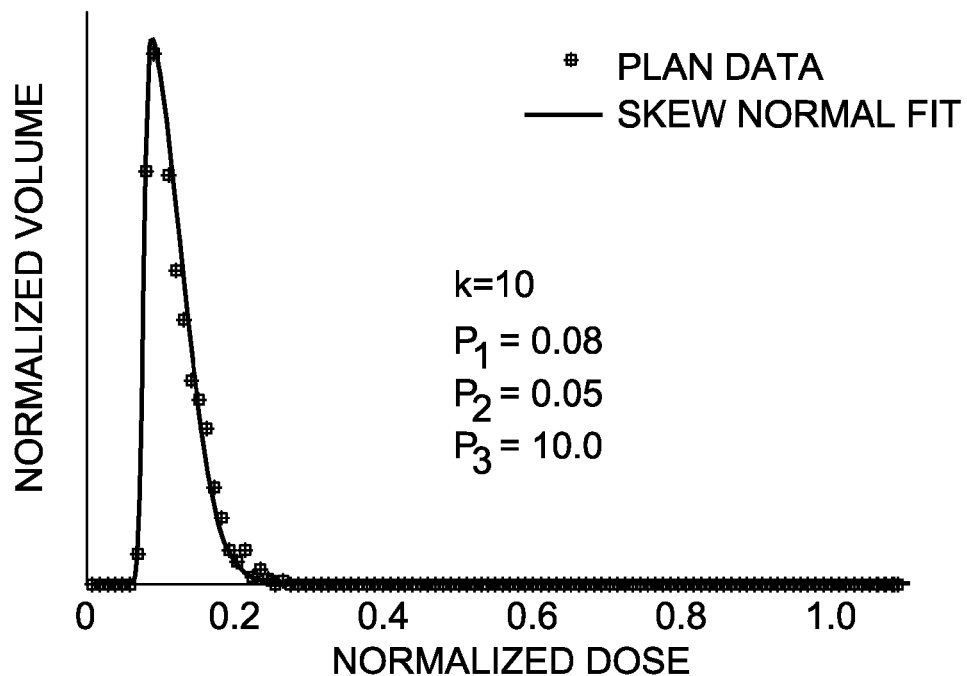

The $\chi_{ijk}$ sub-DVHs depicted in FIG. 5A are idealized distributions. Real clinical distributions will exhibit more variability within a distribution. In FIGS. 6A-6D, rectum sub-volume DVHs $\chi_{ijk}$ for a clinical prostate case are shown for (a) k=0, (b) k=1, (c) k=4, and (d) k=10 at δ=3 mm. The solid curve is a fit to each of the observed sub-DVHs with the skew-normal distribution and its three fitting parameters $p_1$, $p_2$, and $p_3$:

$$f(p_1, p_2, p_3; D) = \frac{1}{\pi p_2} e^{\frac{(D-p_1)^2}{2p_2^2}} \int_{-\infty}^{\frac{p_3(D-p_2)}{p_2}} e^{-\frac{t^2}{2}} dt \quad (5)$$

Equation 5 employs three fitting parameters: $p_1$ (location), $p_2$ (scale), and $p_3$ (shape). One practical limitation of using the skew-normal distribution as the basis function for a differential DVH is that Equation 5 is normalized on the interval from −∞ to +∞, while a DVH is only defined from 0 to +∞. This is readily alleviated by a renormalized skew-normal distribution, $\Phi(p_1, p_2, p_3; D)$, given by Equation 6 below.

$$\phi(p_1, p_2, p_3; D) = \frac{f(p_1, p_2, p_3; D)}{\sum_{D=0}^{\infty} f(p_1, p_2, p_3; \tilde{D})} \quad (6)$$

Whether a single fitting function with a finite set of parameters is capable of modeling $\chi_{ijk}$ for all k will be determined by concordance to the observed training sets. The renormalized skew-normal distribution is but one possible universal fitting function that may be described by a general function $\Phi(p_1, p_2 \ldots p_Q; D)$ with q=1 ... Q parameters $p_Q$. As each OAR for each patient will be fit with this function, the fitting function for each individual $\chi_{ijk}$ will be given by Equation 7, below.

$$\chi_{ijk,fit}(D) = \Phi[p_{ijk1}, p_{ijk2} \ldots p_{ijkQ}; D] \quad (7)$$

After each sub-DVH fit is obtained, e.g. via least-squares minimization, the totality of the training sets' geometric and dosimetric relationships is accessible through analysis of the fitting parameters $p_{ijkq}$. Averaging over all training sets gives the mean fitting parameter as shown in Equation 8, as well as any other statistical analyses afforded by the sample size, e.g. standard deviation.

$$\bar{p}_{jkq} - \frac{1}{N} \sum_{i=1}^{K} p_{ijkq} \quad (8)$$

Further, as $p_{ijkq}$ is a direct function of increasing boundary distance through $r_k$ any functional fit (e.g. generalized polynomial) through $\bar{p}_{jkq}$ yields a deterministic trajectory $p_{jq}(k)$ of the $q^{th}$ parameter in the $j^{th}$ OAR. The $p_{jq}(k)$ trajectories in turn yield the resultant predicted DVH for the $j^{th}$ structure in the $i^{th}$ dataset, as shown in Equation 9.

$$V'_{ij,pred} = \sum_{k=0}^{\infty} \Phi[p_{j1}(k), p_{j2}(k), \ldots p_{jQ}(k); D] \cdot V(A_{ijk}). \quad (9)$$

Goodness-of-fit analyses comparing $V'_{ij,pred}$ to the measured $V'_{ij}$ can inform the quality of the ensemble averaging fits in individual cases, as well as identify outliers with respect to the mean, as discussed in more detail below. It is important to stress that the elements of Equation 9 are entirely geometric, while the output distribution is the full does volume histogram of the $j^{th}$ OAR for any patient. As the function $\Phi[p_{j1}(k), p_{j2}(k), \ldots p_{jQ}(k); D]$ represents the mathematical summary of prior experience, this relation and the formalism that led to it illustrates an exemplary embodiment of this disclosure.

In the case of "new" patients, i.e. the introduction of a new dataset for which there is no measured dose matrix $D_{N+1}$, geometric operations alone on $SS_{(N+1)j}$ yield $A_{(N+1)jk}$ and $V(A_{(N+1)jk})$, which in turn may be employed in Equation 9 to obtain a predicted DVH for any structure with an associated function $\Phi[p_{j1}(k), p_{j2}(k), \ldots p_{jQ}(k); D]$. A predicted DVH, informed by the N prior cases, is thus available for any new dataset even in the absence of any dosimetric information as long as the clinical goals are identical to the training sets.

To validate this formalism, clinically-approved treatment plans for intact prostate IMRT and head & neck IMRT were utilized as training data to develop models that generate predictive DVHs for rectum, bladder, and parotid glands. A general framework outlined in this section was repeated for each OAR. Obtaining predictive DVHs for a given OAR is achieved by six distinct steps which include: 1) data acquisition, 2) dose-to-distance modeling, 3) fitting of parameter trajectories, 4) model validation, 5) outlier identification, and 6) model refinement.

N site-similar patients were randomly identified from our clinical database. Each site-similar IMRT treatment plan was clinically approved according to the same institutional planning goals (shown in Table 1), and consisted of a structure set ($SS_{ij}$) and a dose matrix ($D_i$) with 3 mm×3 mm×3 mm voxel size that was developed with a commercial treatment planning system (Pinnacle³, a product of Philips Medical Systems of Andover, Mass.).

Figure 7:
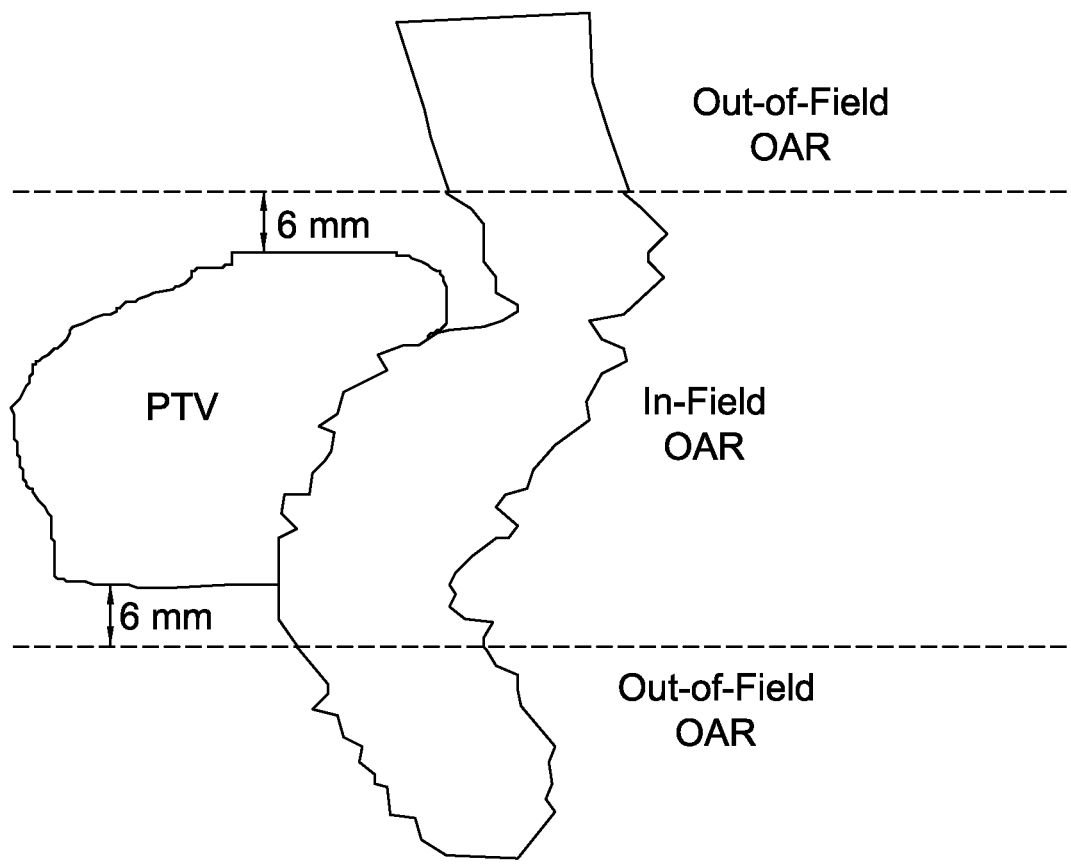
FIG. 7 is a graph depicting a representation of in-field and out-of-field OAR for prostate and rectum, a geometric distinction important in co-planar radiotherapy deliveries.

IMRT delivery on conventional linear accelerators is typically accomplished using co-planar beam arrangements. Co-planar delivery violates the isotropic assumptions inherent to the scalar boundary distance formalism because the negative dose gradient underneath collimating jaws is intrinsically greater than the in-field dose gradient achieved via intensity modulation. To restore the central assumptions of this work, the in-field portion of the OAR was considered separately from the out-of-field portion of the OAR, as shown in FIG. 7. Alternate embodiments may instead focus on the orientation components of the boundary distance vectors, an approach that may obviate the need for the in-field and out-of-field designations.

Figure 8A:
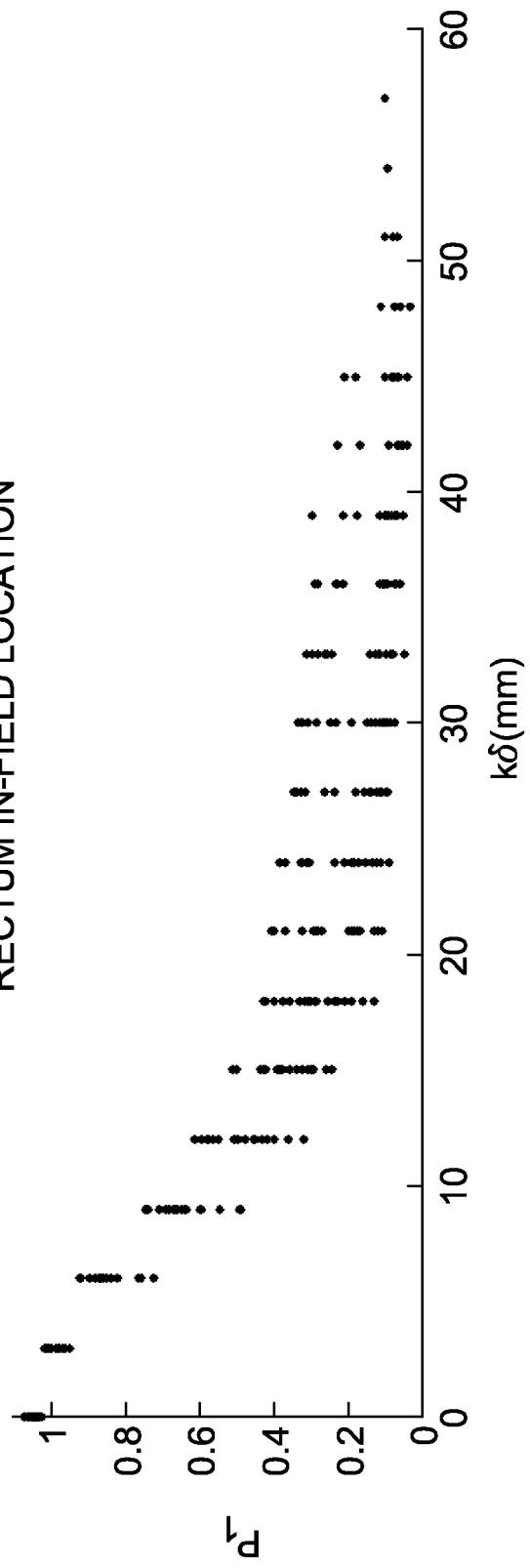
FIG. 8A-8F are depicting in-field rectum parameters and fitting.
Figure 8B:
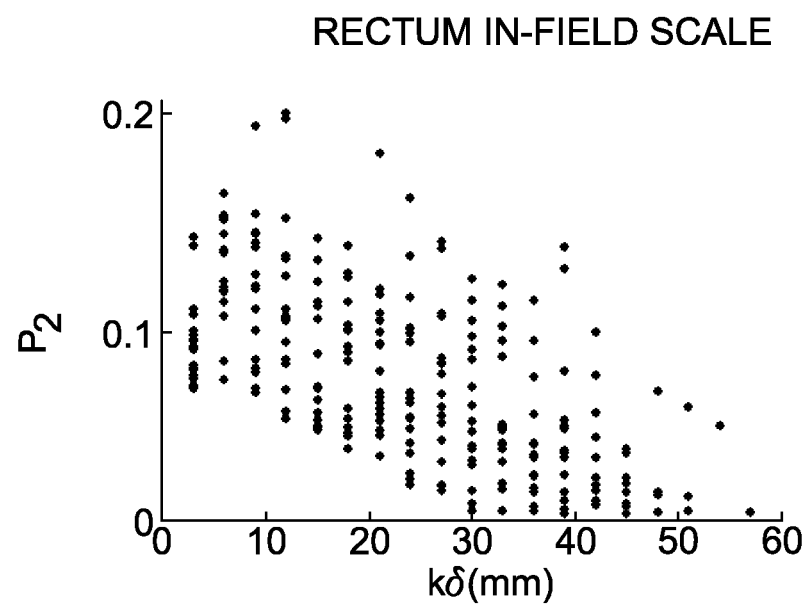
Figure 8C:
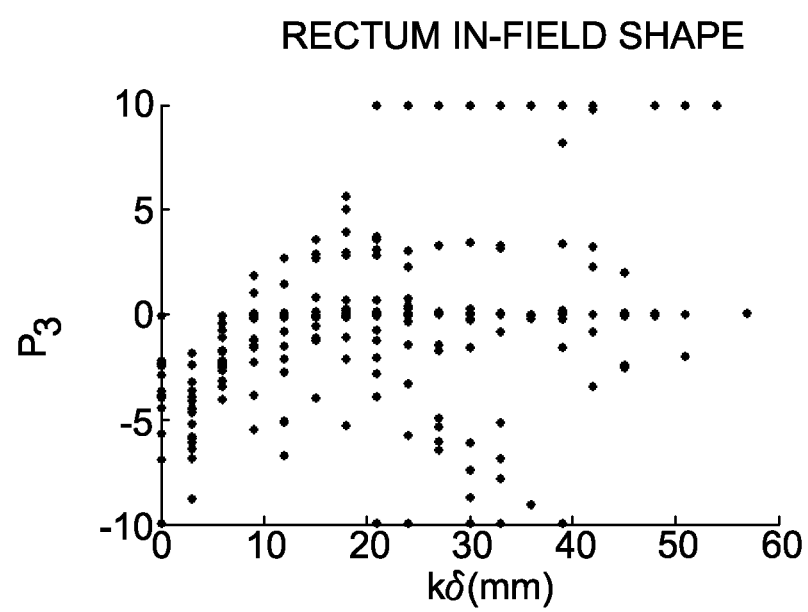
Figure 8D:
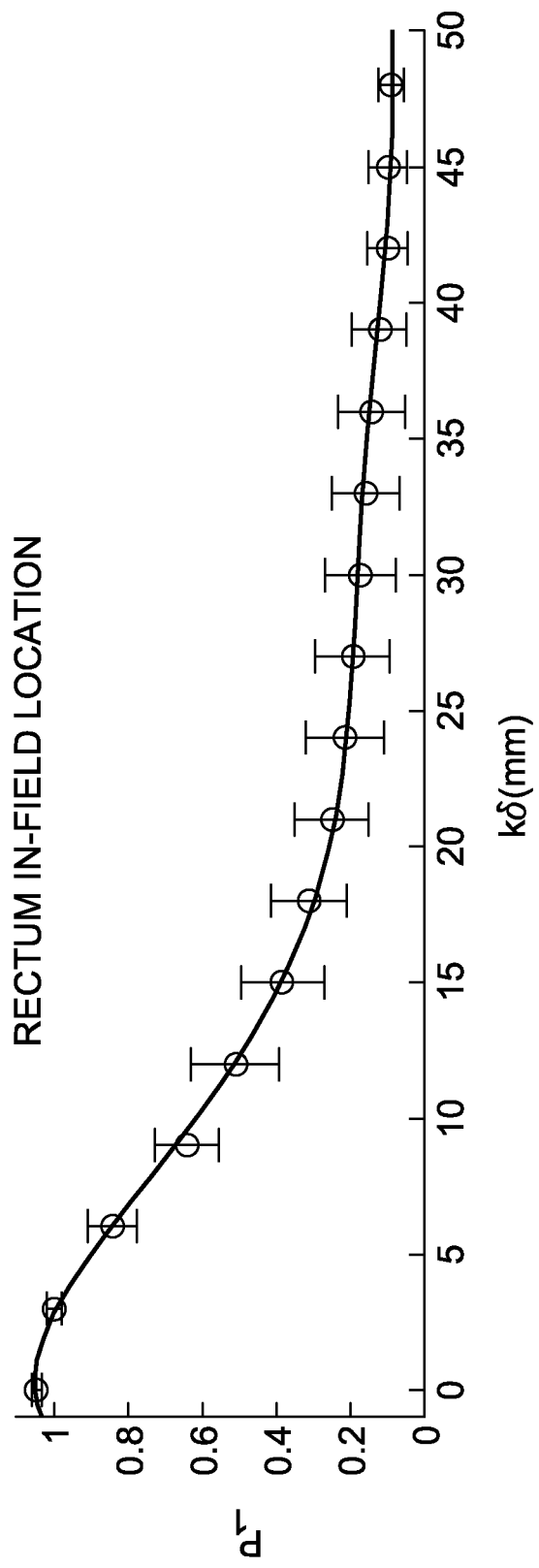
Figure 8E:
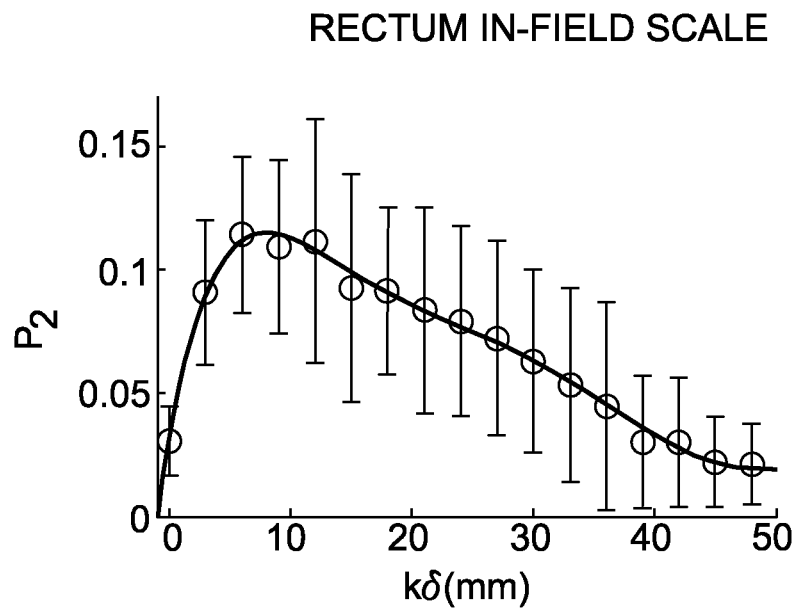
Figure 8F:
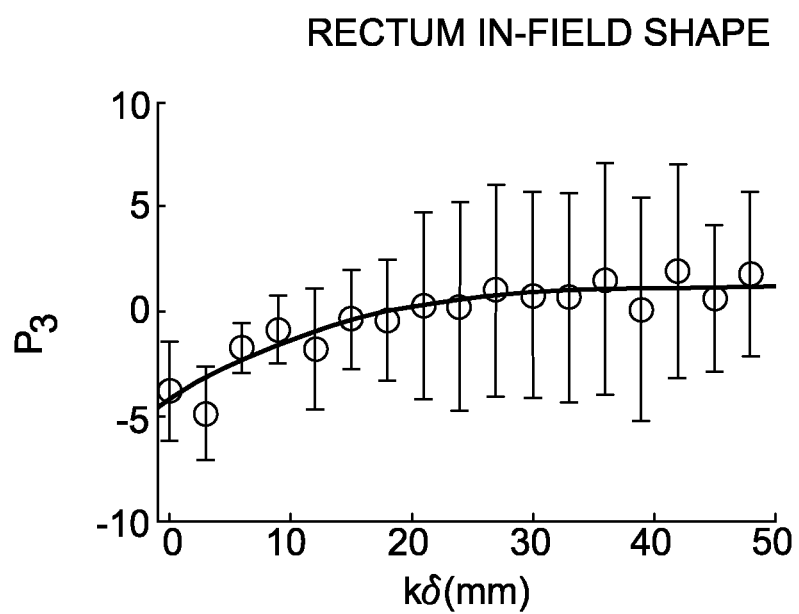

More specifically, FIGS. 8A-8C illustrate a distribution of in-field rectum parameters for all training sets. FIGS. 8D-8F illustrate a fitting $\bar{p}_{jkq} \pm SD_{jkq}$ with generalized polynomial function. Each OAR model thus contains two models, in-field and out-of-field, that are summed to give the final predictive DVH, as shown in Equation 10 below.

$$V'_{ij,pred} = \sum_{k=0}^{\infty} \begin{bmatrix} \Phi[p_{j1}^{IN}(k), p_{j2}^{IN}(k), \ldots p_{jQ}^{IN}(k); D] \cdot V(A_{ijk}^{IN}) + \\ \Phi[p_{j1}^{OUT}(k), p_{j2}^{OUT}(k), \ldots p_{jQ}^{OUT}(k); D] \cdot V(A_{ijk}^{OUT}) \end{bmatrix} \quad (10)$$

The renormalized skew normal distribution given by equation 5 was employed as a candidate fitting function for all sites, training sets, and OARs explored. This probability distribution function was used to determine three parameters, location ($p_1$), scale ($p_2$), and shape ($p_3$), via least-squares minimization for all $\chi_{ijk}$.

A mean fitting parameter $\bar{p}_{jkq}$ for each PTV shell is obtained by averaging each parameter $p_{ijkq}$ over all training sets for both the in-field and out-of-field OAR. Statistical noise for the sample is assessed through determining the standard deviation of the data used to calculate all mean fitting parameters, as shown in Equation 11 below.

$$SD_{jkq} = \sqrt{\frac{1}{N-1}(p_{ijkq} - \bar{p}_{jkq})^2} \quad (11)$$

shown as error bars in FIGS. 8C-8F.

Plotting the mean fitting parameter for location ($p_1$) as a function of distance for both the in-field and out-of-field OAR provides insight into the manner by which the dose in each shell changes as a function of kδ. Similarly, plotting the mean fitting parameter for scale ($p_2$) as a function of kδ for both the in-field and out-of-field OAR provides insight into the spread or variation of dose values in each shell. Finally, plotting the mean fitting parameter for shape as a function of kδ provides insight into how the shape of the sub-DVH changes as a function of distance (i.e. is the tail of the distribution pointed toward low-dose or high-dose). The shape parameter ($p_3$) was only allowed to vary between [−10,10] since values outside of this range result in minimal effect on the shape of the distribution.

A generalized polynomial of order B was employed to fit the evolution of the $\bar{p}_{jkq}$ parameters, as shown in Equation 12 below, $$p_{jq}(k) = \sum_{b=1}^{B} \alpha_{jqb} \cdot (k\delta)^b \quad (12)$$

where the maximal order B was chosen on a case-by-case basis and the coefficients $a_{jqb}$ were determined through least-squares minimization. Each $\bar{p}_{jkq}$ for a given k is weighted by $$w_{jkq} = \frac{1}{SD_{jkq}}.$$

The function $p_{jq}(k)$ accounts for any mean fitting parameters at a given k that may be statistical outliers. FIGS. 8D-8F display examples of the $p_{jq}(k)$ fits set against $\bar{p}_{jkq}$ (open circles) and $SD_{jkq}$ (error bars) for the in-field rectum cohort.

In order to assess the efficacy of the developed model on new patient data, predictive DVHs were obtained for an independent set of validation patients that were not part of the training data cohort. The accuracy of the model was assessed by comparing each predicted cumulative DVH, $DVH_{ij,pred}(D)$, to the clinically-approved plan's cumulative DVH, $DVH_{ij}(D)$. Comparing cumulative DVHs is preferred at this stage because of their connection to established clinical endpoints. Were $DVH_{ij,pred}(D)$ a fit to $DVH_{ij}(D)$ standard goodness-of-fit analyses such as chi-squared tests would be appropriate. However, as the employed curve-fitting methods described leave no degrees of freedom at this stage, it becomes more difficult to quantify the discrepancy between the predicted DVH and the clinical DVH in a meaningful way. A singular value that measures this discrepancy can be found in the sum of residuals, as shown in Equation 13 below $$SR_{ij} = \sum_{D=0}^{\infty} \varepsilon_{ij}(D) \quad (13)$$

where $$\varepsilon_{ij}(D) - [DVH_{ij}(D) - DVH_{ij,pred}(D)] \cdot \Delta D \quad (14)$$

with the dose bin size included in the product to eliminate bin size dependence. More traditional error analyses employ sums of squared residuals, but this is not appropriate here as negative residuals (clinical plan bettering the prediction at a given dose) are not on equal footing with positive residuals (prediction bettering clinical plan at a given dose).

As a major goal of the predictive DVH methodology is the identification of sub-optimal plans, it is important to separate the outlier identification task from any goodness-of-fit analysis used for model validation. As the sum residuals makes no distinction between positive $\varepsilon(D)$ values (predicted DVH betters the clinical DVH), and negative $\varepsilon(D)$ values (clinical DVH betters the predicted DVH), the identification of sub-optimal plans was accomplished by use of a restricted sum of residuals, as shown in Equation 15 below, $$RSR_{ij} = \sum_{D=0}^{\infty} \varepsilon_{ij}^{+}(D) \quad (15)$$

where $$\varepsilon^{+}(D) = \begin{cases} \varepsilon(D), & \text{if } \varepsilon(D) > 0 \\ 0, & \text{if } \varepsilon(D) \leq 0 \end{cases}. \quad (16)$$

Figure 9A:
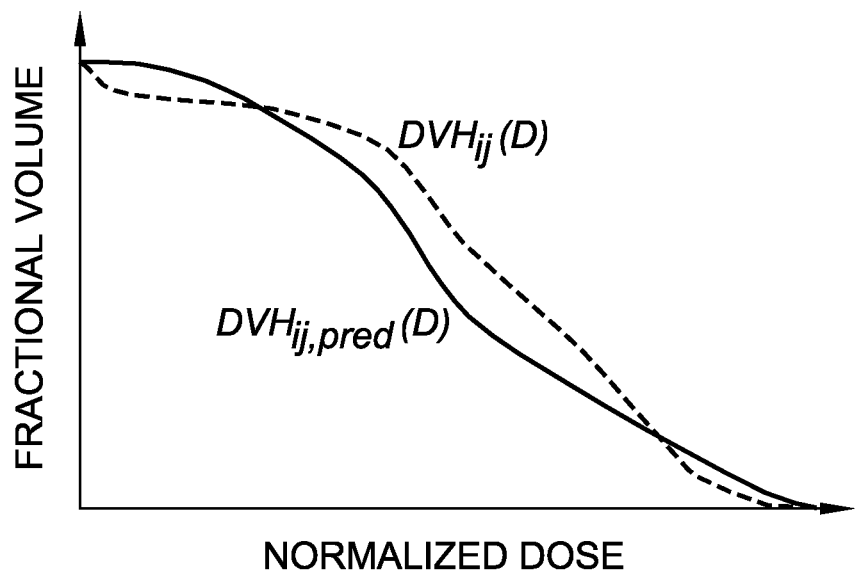
FIGS. 9A-9C are graphs depicting goodness-of-fit and outlier identification analyses using analysis of the cumulative DVHs.
Figure 9B:
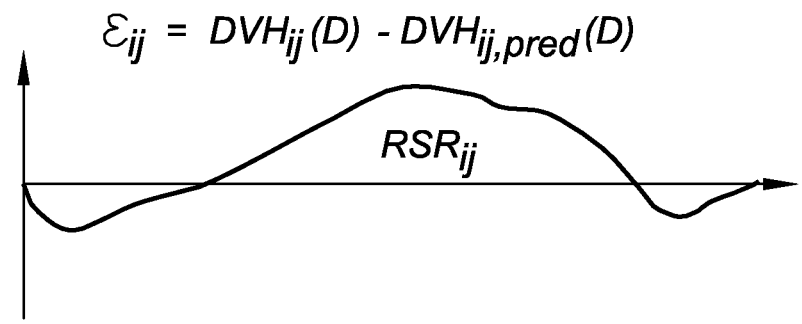
Figure 9C:
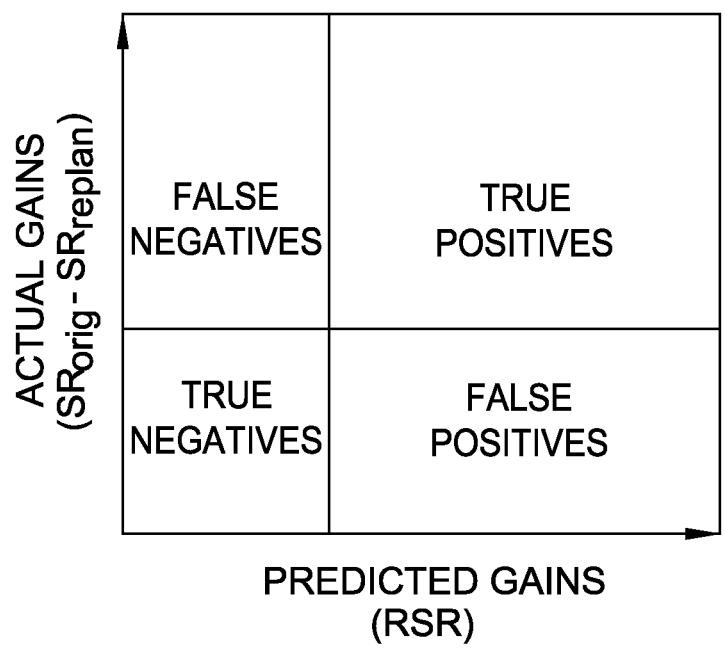

A schematic of both the goodness-of-fit analysis and the outlier identification analysis can be seen in FIGS. 9A-9C. Large values of $RSR_{ij}$ signal a patient for which the clinical DVH exceeds the predicted DVH by a considerable amount compared to other site-similar treatment plans, and thus serves as a surrogate for the identification of clinical DVHs that appear to have sub-optimal OAR sparing.

The planning process for these patients was repeated ("re-planning") to establish the true limit of OAR sparing. During re-planning, care was taken to hold constant or improve PTV dosimetric aspects and maintain all other OAR DVH sparing within the dosimetric objective list in Table 1. A refined model was obtained by repeating the modeling process as described above on the training data sets that remain after excluding the correctly identified sub-optimal plans. This refined model was again evaluated on the same set of independent validation patients. Analysis of the sum of squared residuals was completed both before and after model refinement.

Figure 10A:
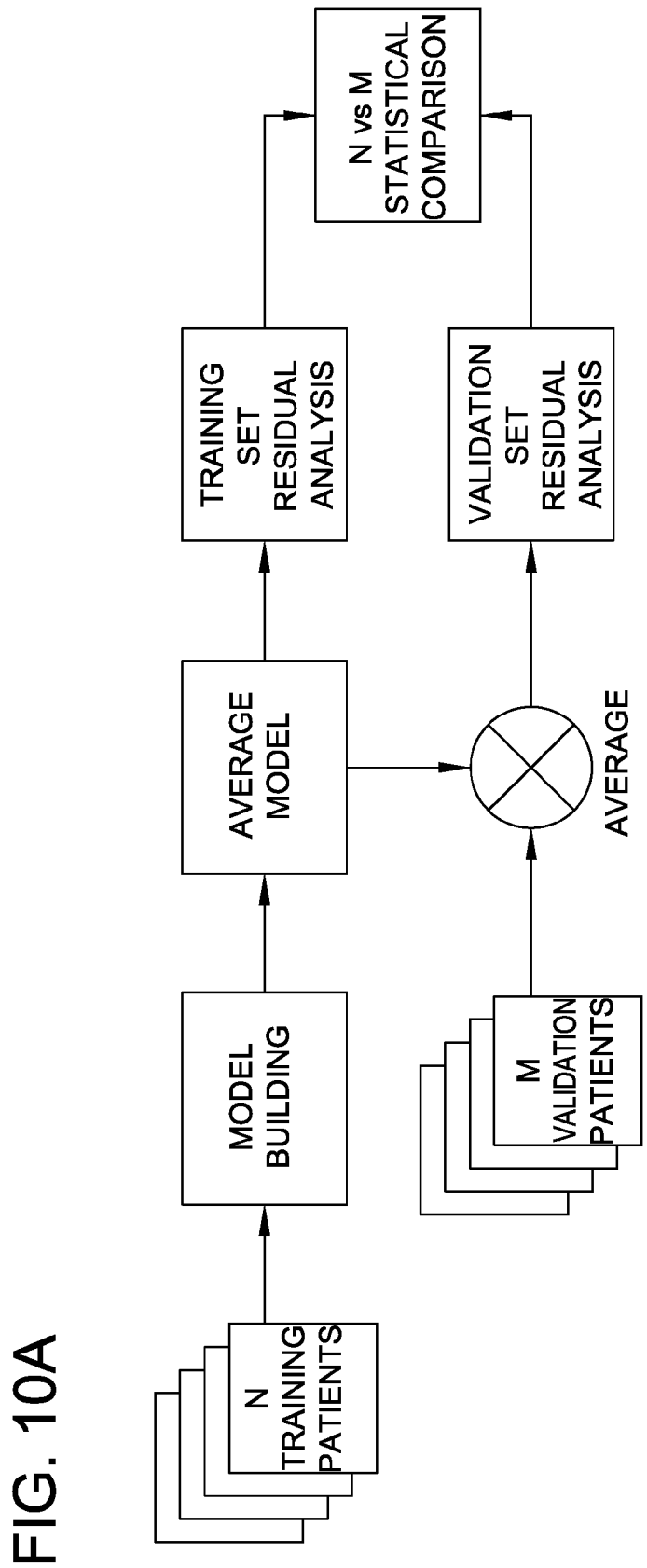
FIGS. 10A and 10B are block diagrams depicting a two-stage validation of predictive DVH modeling.
Figure 10B:
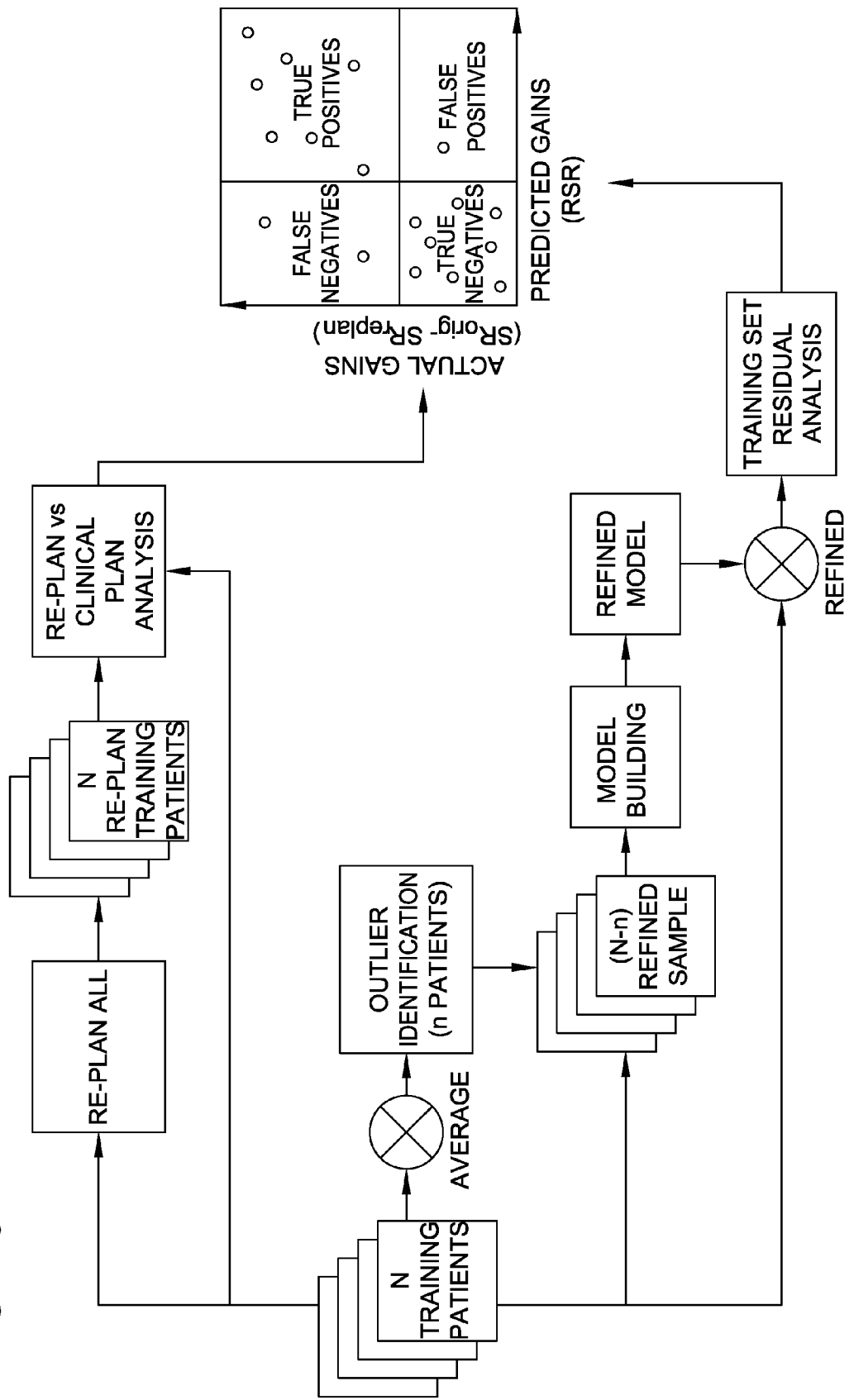
Figure 11A:
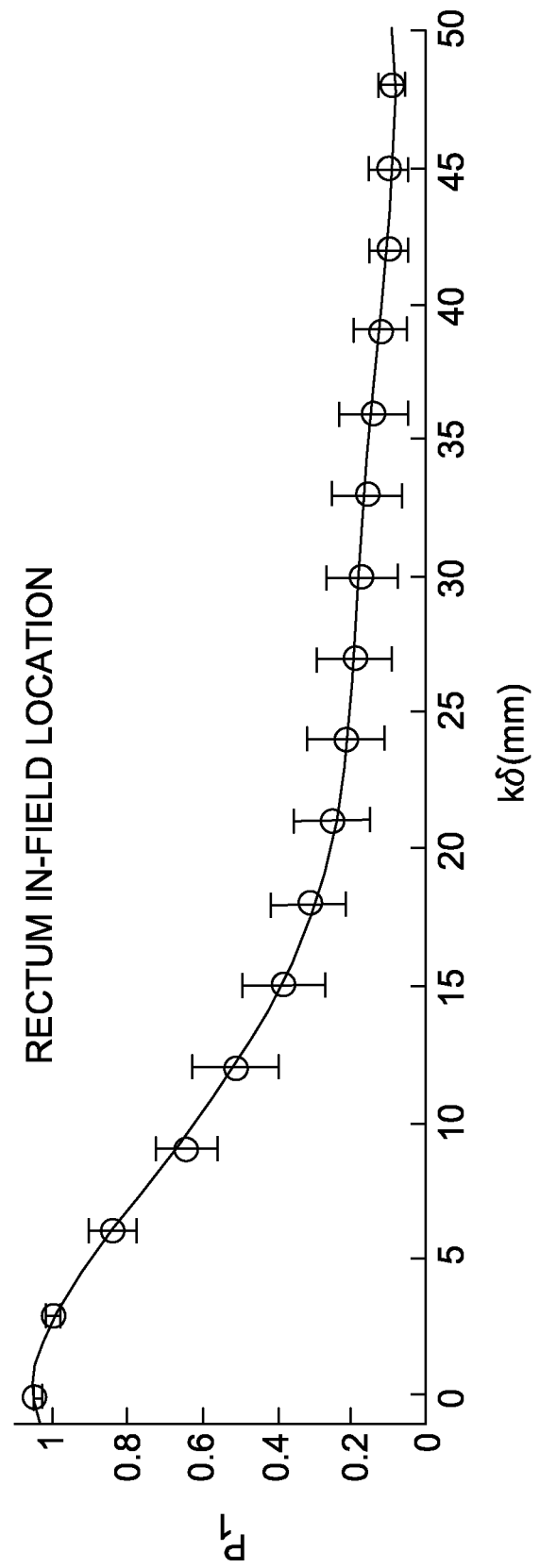
FIGS. 11A-11L are graphs depicting distribution of parameters and generalized polynomial fits for rectum and bladder in intact prostate IMRT with a 20-patient training cohort.
Figure 11B:
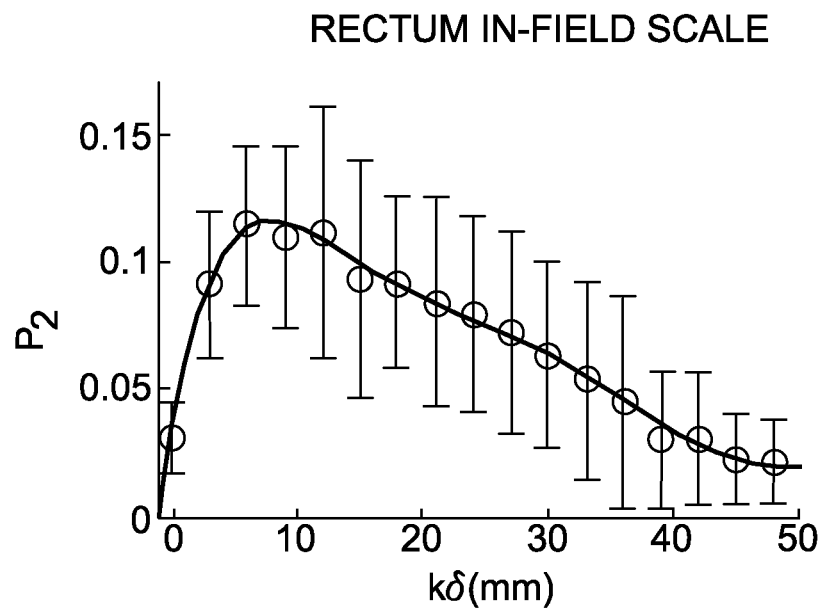
Figure 11C:
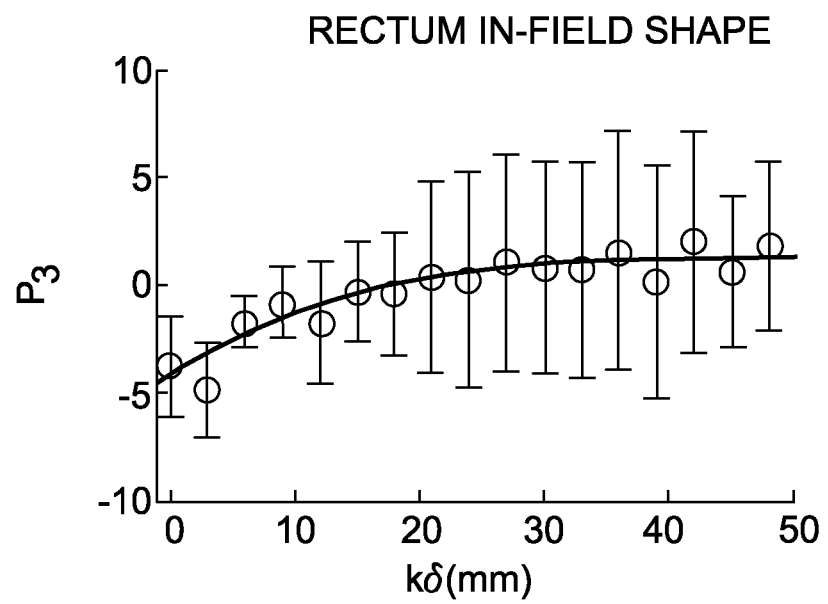
Figure 11D:
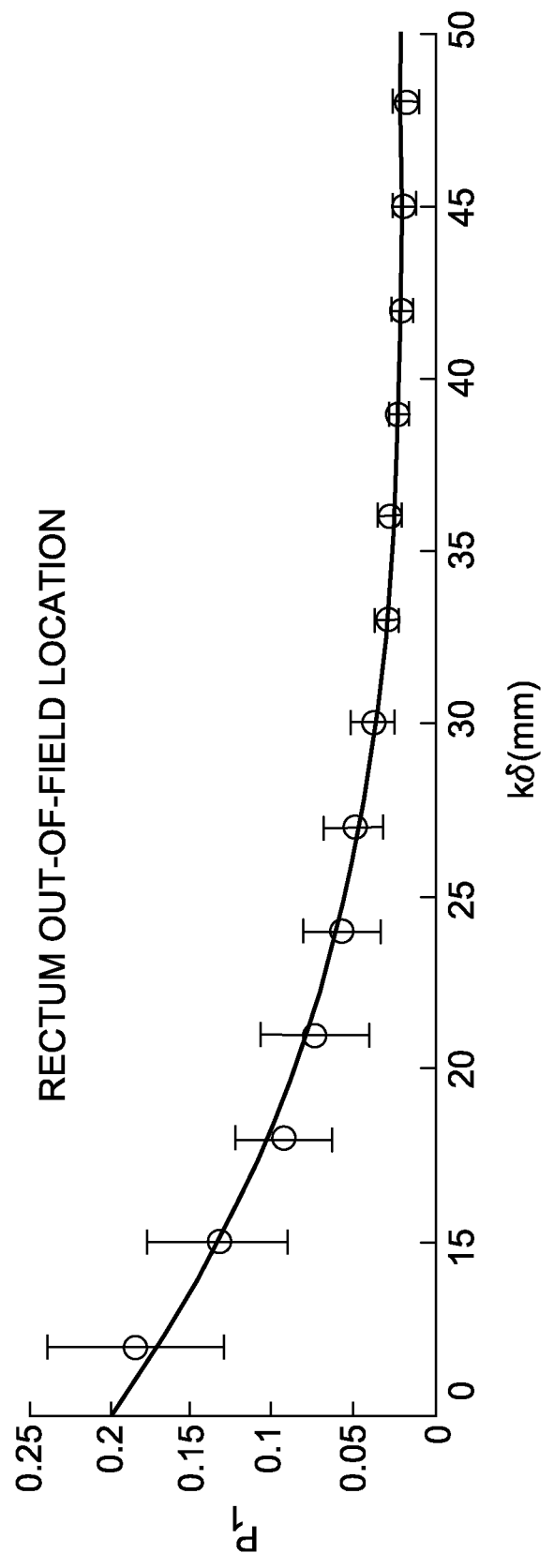
Figure 11E:
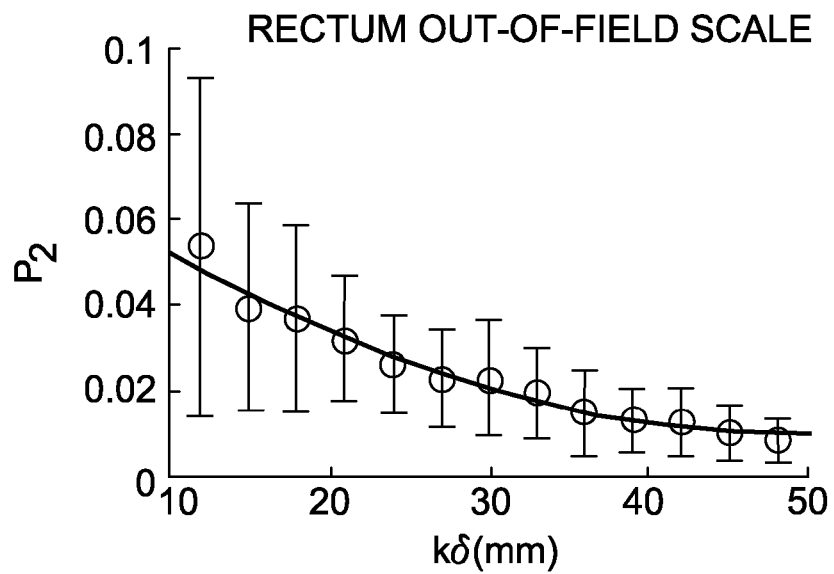
Figure 11F:
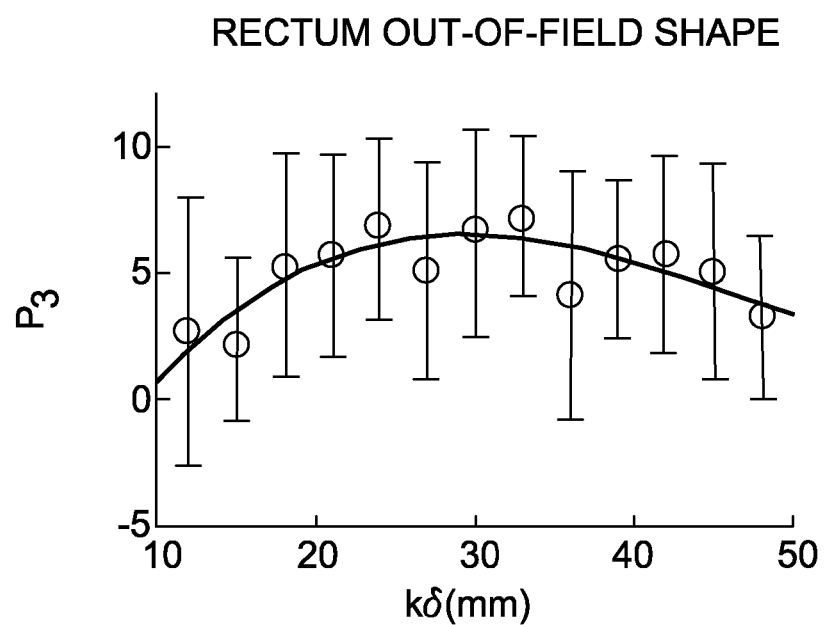
Figure 11G:
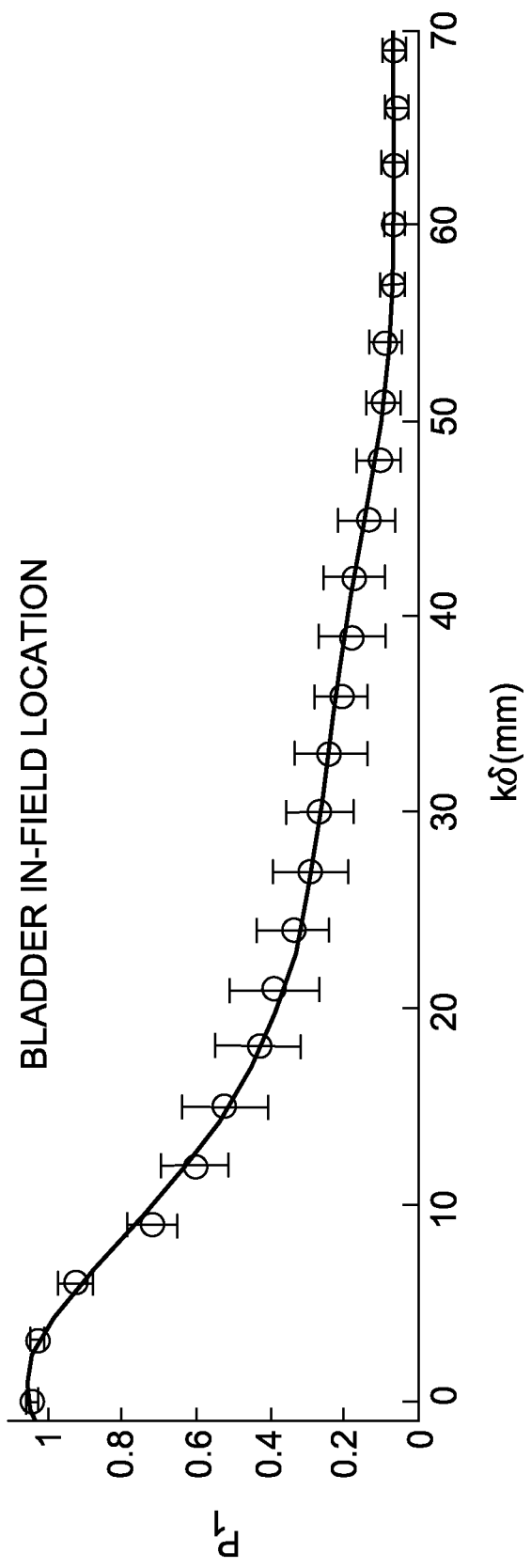
Figure 11H:
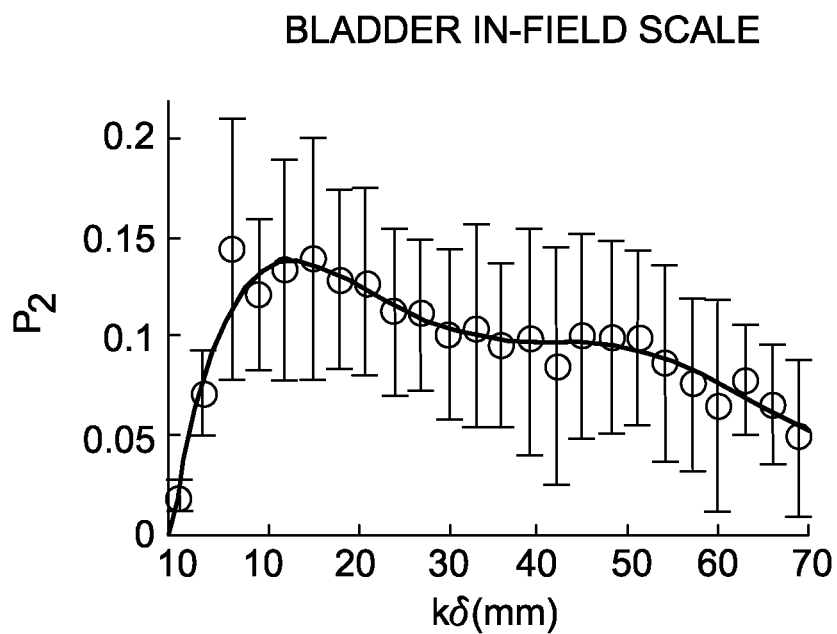
Figure 11I:
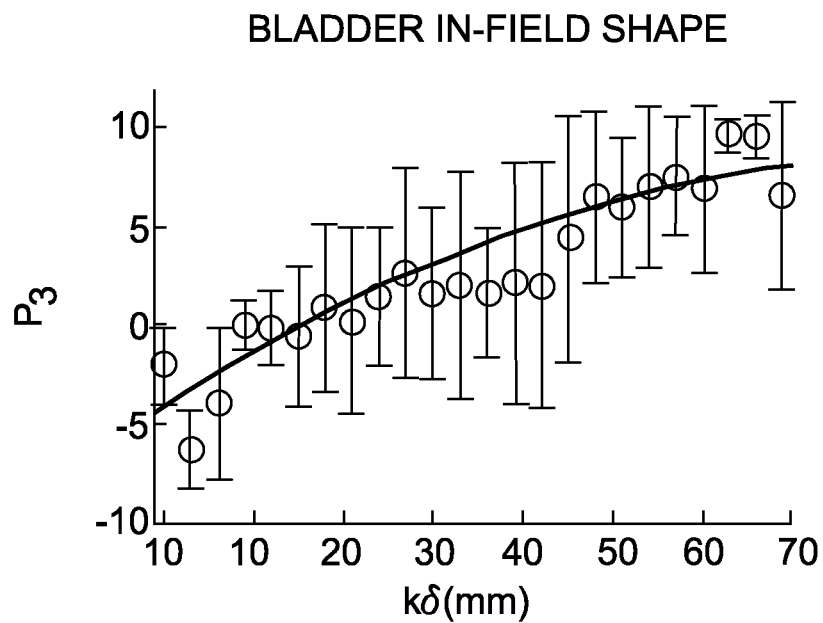
Figure 11J:
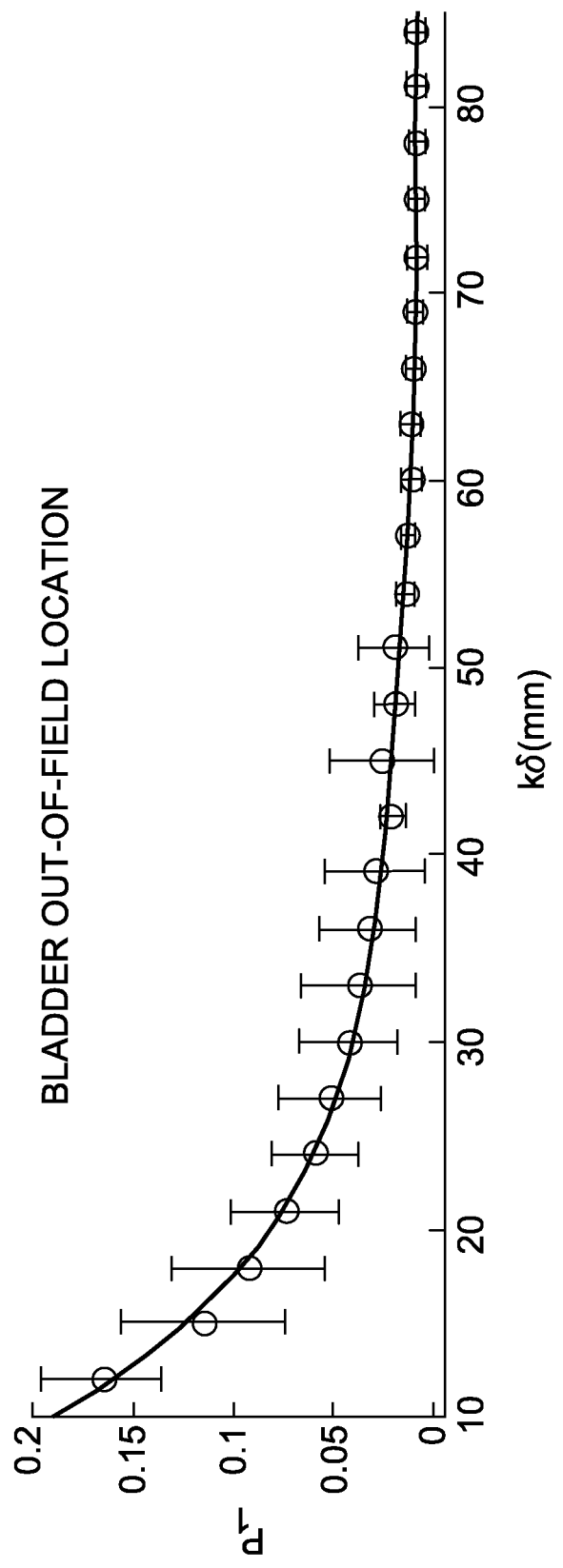
Figure 11K:
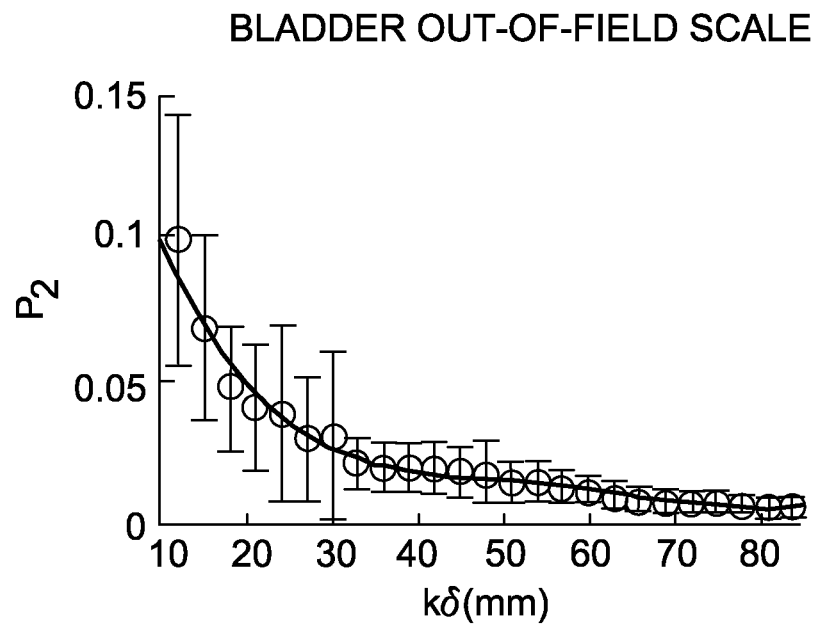
Figure 11L:
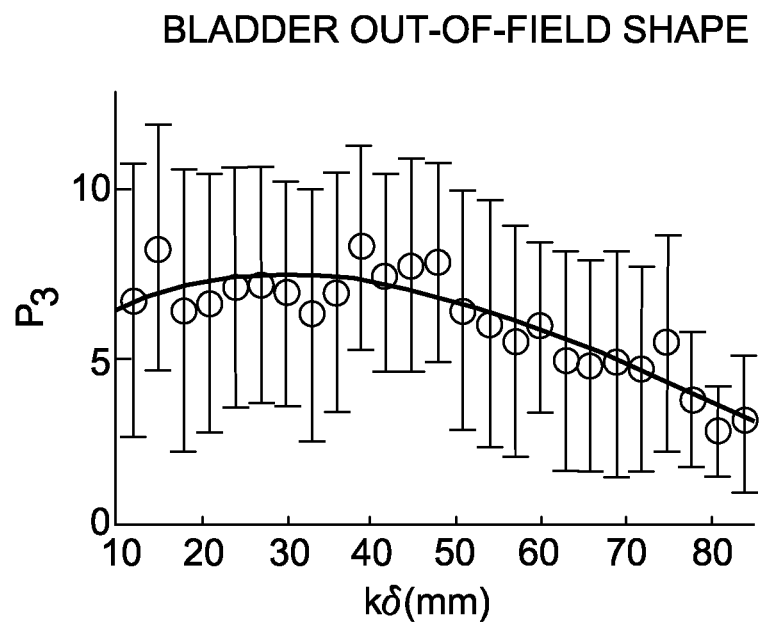

FIGS. 10A and 10B illustrate two-stage validation of predictive DVH modeling. FIG. 10A shows an AVERAGE model that is trained with N clinical patient plans. The accuracy of the AVERAGE model is analyzed both by an analysis of its performance on the training data as well as its ability to correctly predict the DVHs of an equivalent sample of M patients in a sequestered validation set. Equivalent performance between training and validation sets confirms the ability of modeling process to substantially accurately predict DVHs. FIG. 10B shows use of the AVERAGE model on the training data sample, outliers with relatively high RSR (Equation 15) are identified as potentially sub-optimal plans. The modeling process is repeated without inclusion of these outliers, yielding the REFINED model. The predicted DVH gains per patient are represented by the RSR values obtained in application of the REFINED model to the entire training sample. Verifying the predicted gains was accomplished by careful re-planning of each of the training patients in an attempt to increase organ sparing. Quantitative comparison between the re-plan DVHs and the original DVHs was accomplished by computing the sum of residuals between them, removing the predicted DVH results entirely from this quantity.

Since each OAR has a finite size and a finite number of patients were used to develop each model, our statistics decrease for points at large distances from the PTV. Therefore, at a determined distance from the PTV where the OAR statistics become sparse, the mean parameter trajectory fits were held at a constant value. These constants varied for each organ depending on the number of patients with non-zero volume of OAR in each PTV ring.

Twenty intact prostate patients treated with IMRT were used to obtain predictive DVH models for the rectum and bladder, denoted as the initial AVERAGE model. For both bladder and rectum respectively, five patients out of the initial twenty patient cohort were identified as outliers and removed from the training set to develop the REFINED model. FIGS. 12A-12F demonstrates both AVERAGE and REFINED models' DVH predictions against three clinically-approved plans for both bladder and rectum. Both demonstrate good concordance, but the REFINED model more closely matches the observed DVHs.

FIGS. 14A-14F show the identification of sub-optimal plans in the training cohort by the AVERAGE model and the demonstration through re-planning of the realized improvements.

FIGS. 15A-15F are graphs demonstrating the concordance of the two predictive DVH models to the clinically-approved rectum and bladder DVHs from the validation set, i.e. "new" plans unseen by the model.

Figure 13A:
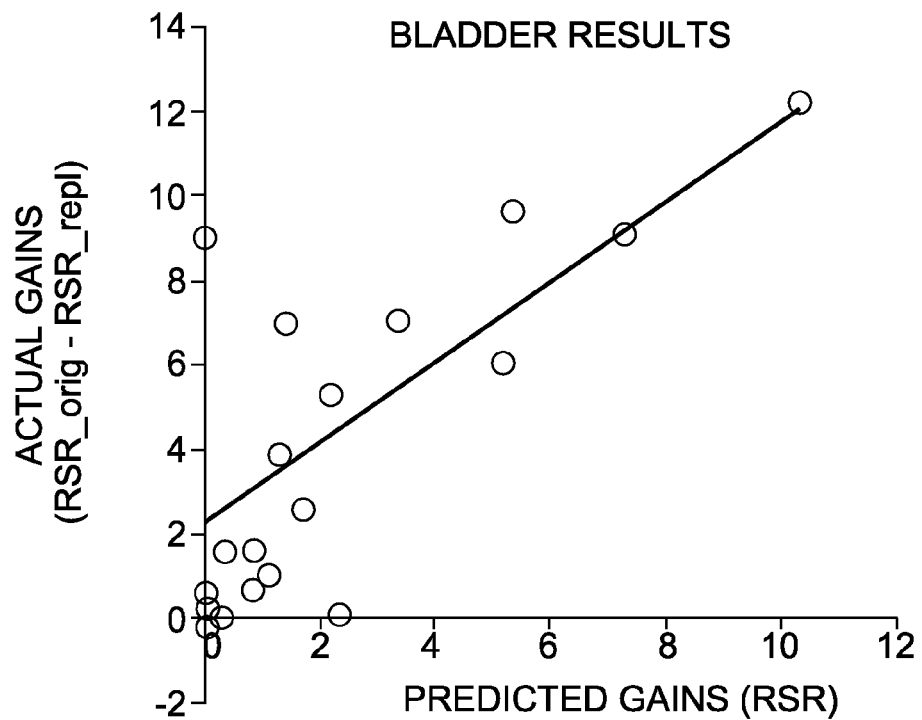
FIGS. 13A and 13B are graphs depicting correlation between predicted gains and gains realized through re-planning, validating the rectum and bladder models' ability to correctly distinguish optimal and sub-optimal treatment plans.
Figure 13B:
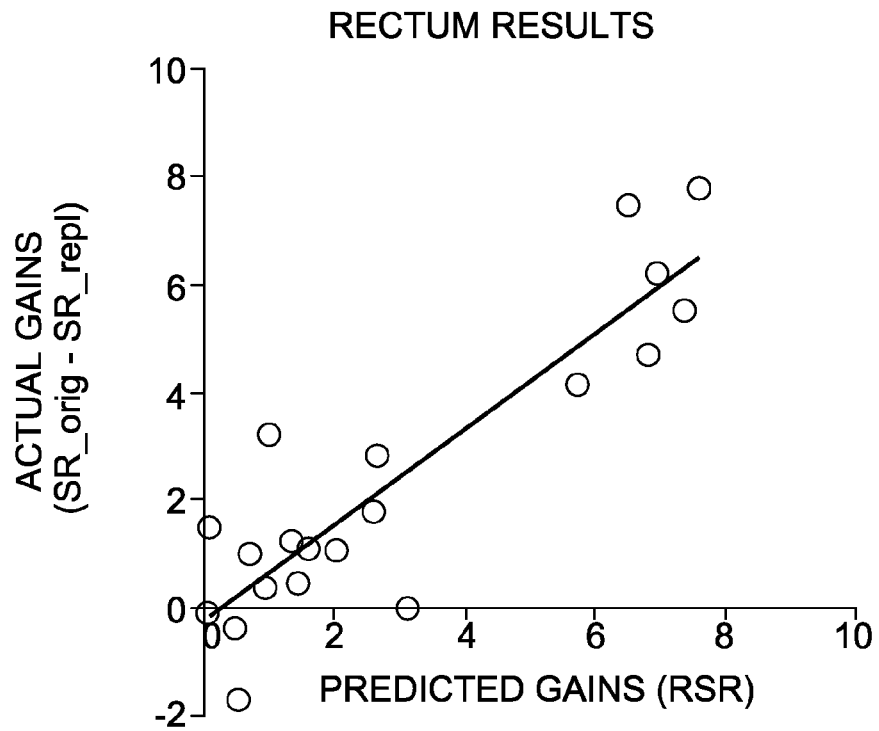
Figure 14A:
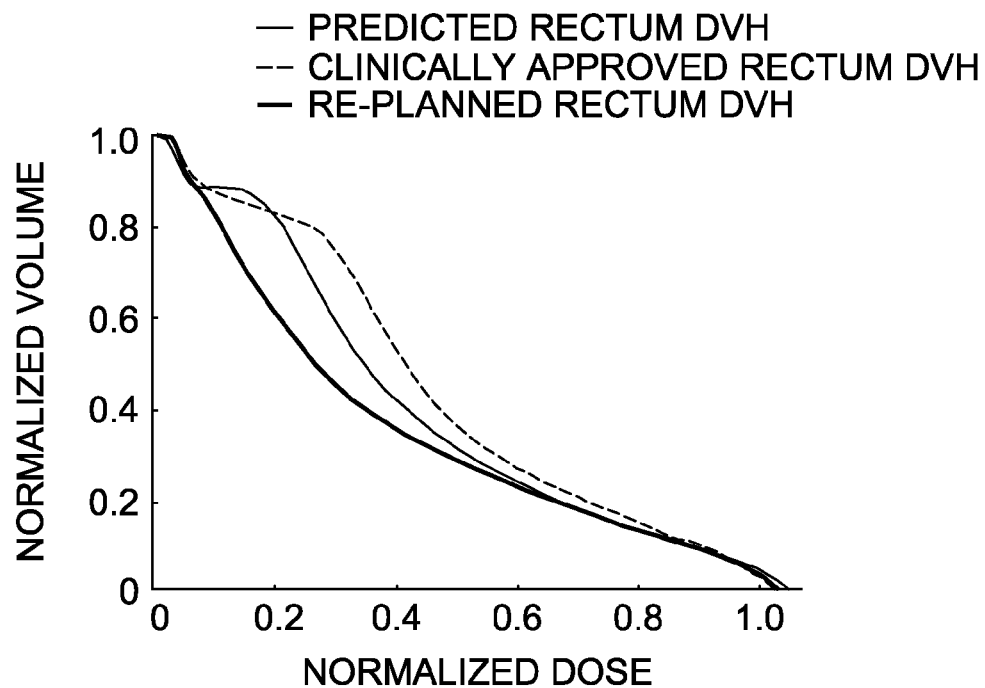
FIGS. 14A-14F are graphs depicting predicted rectum and bladder DVHs correctly identifying plans that could be improved under replanning.
Figure 14B:
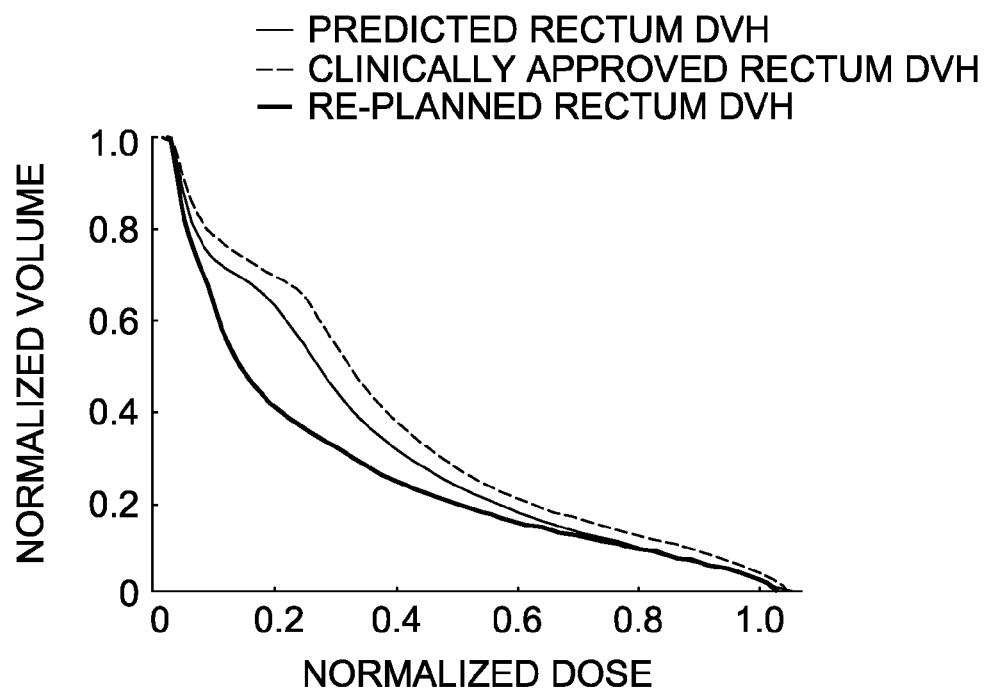
Figure 14C:
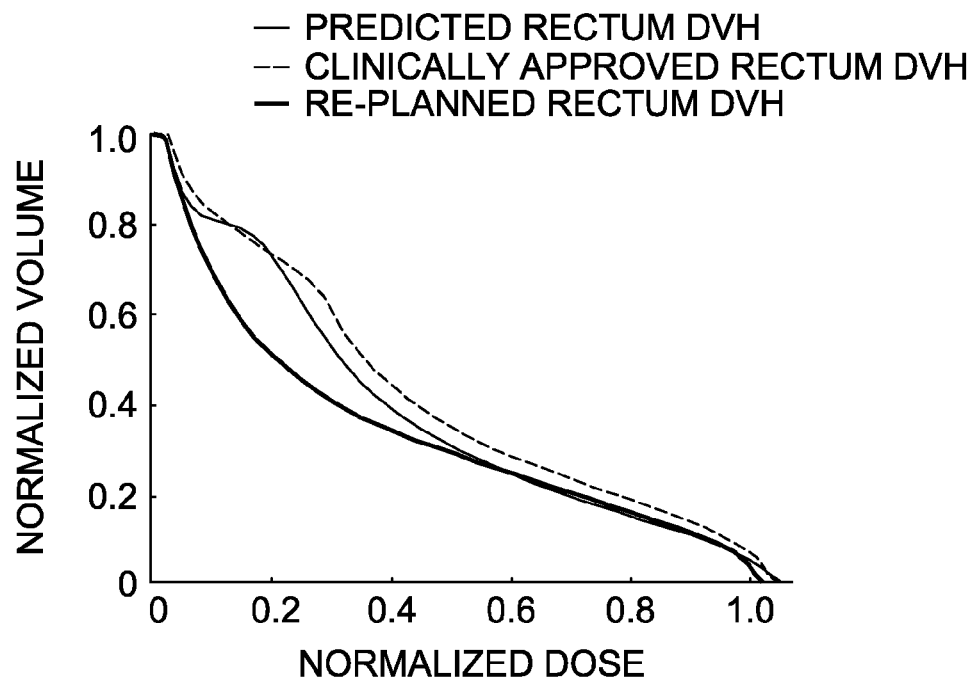
Figure 14D:
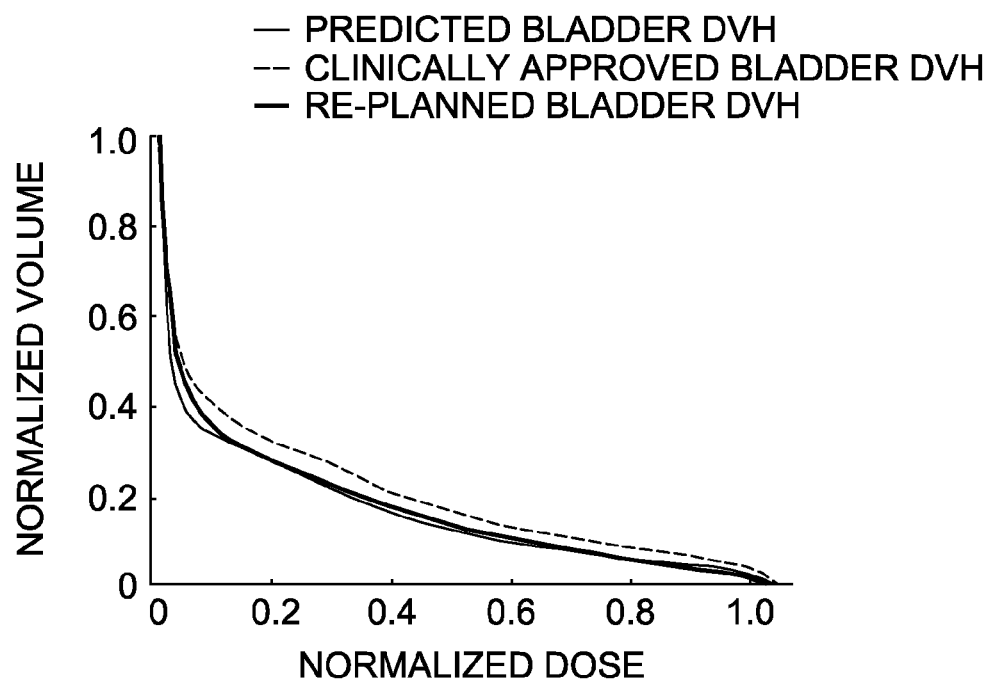
Figure 14E:
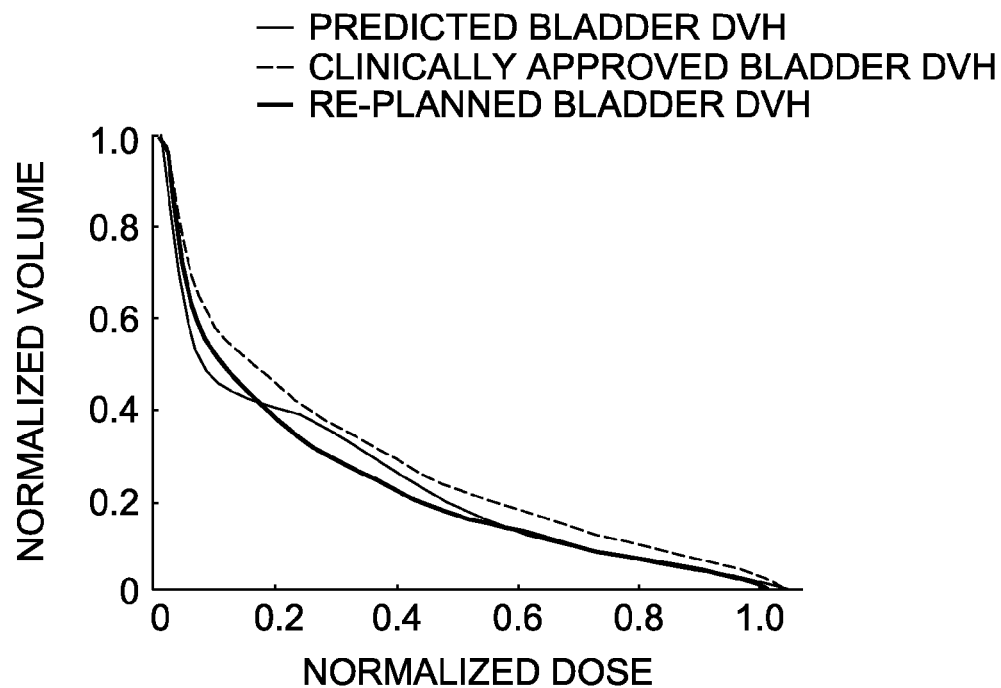
Figure 14F:
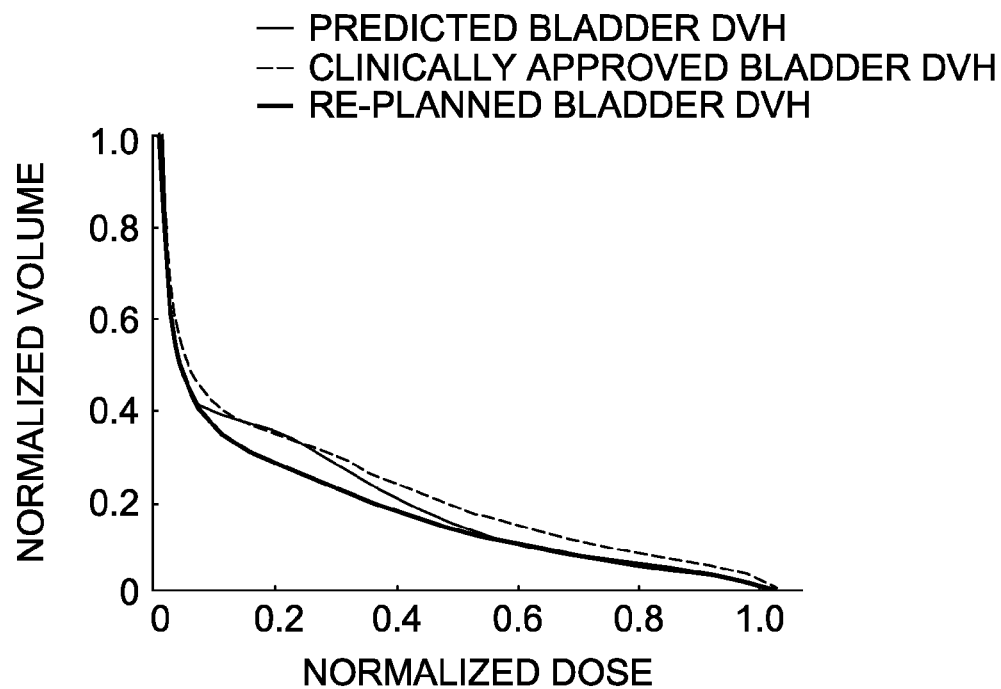
Figure 15A:
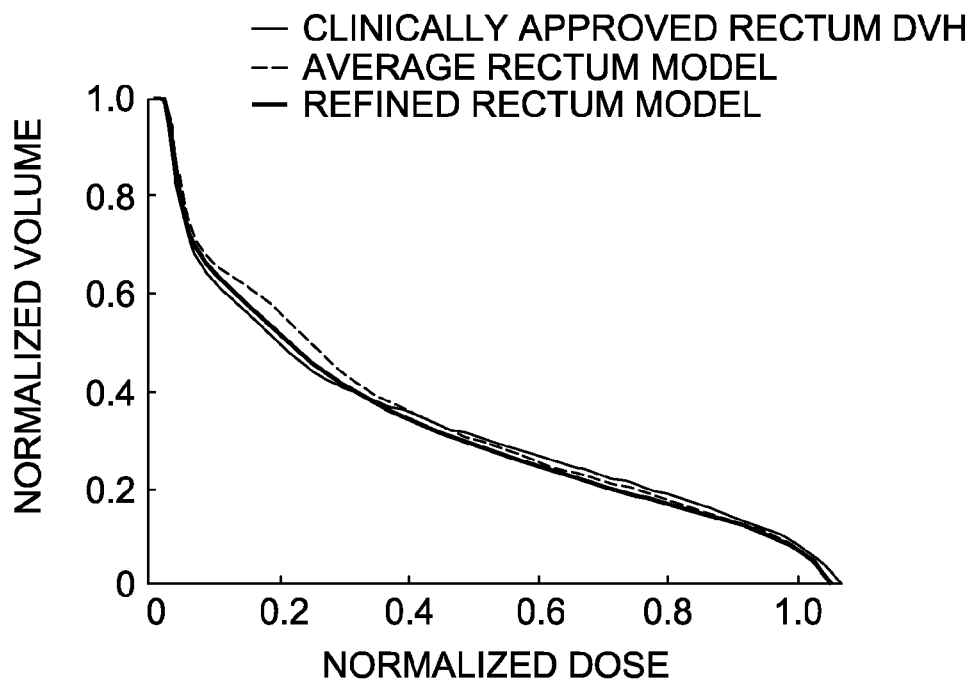
FIGS. 15A-15F are graphs demonstrating the concordance of two predictive DVH models to the clinically-approved rectum and bladder DVHs from the validation set, i.e. "new" plans unseen by the model.
Figure 15B:
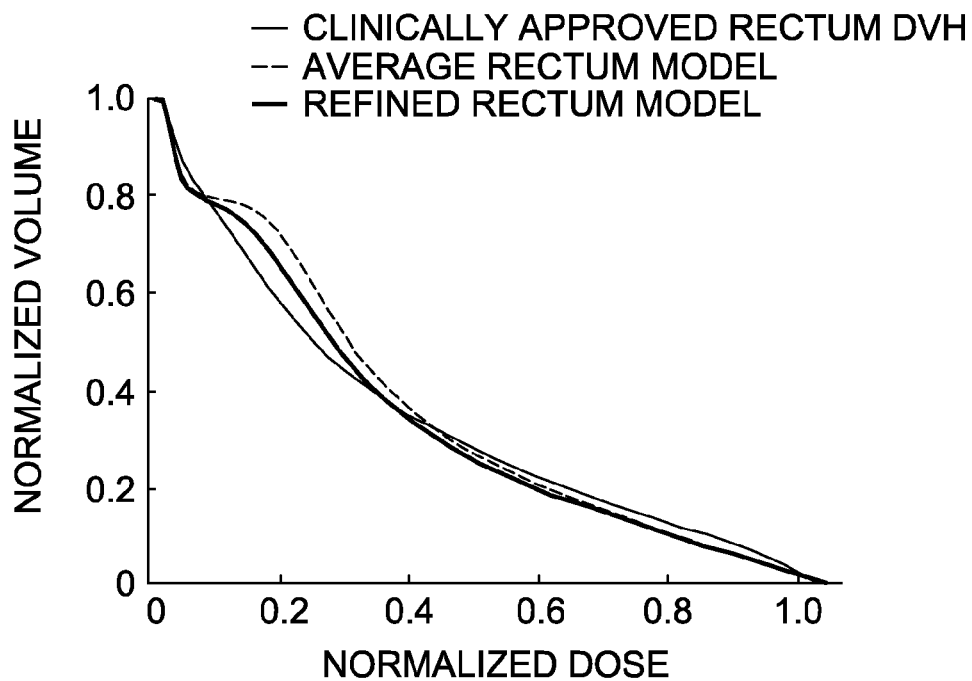
Figure 15C:
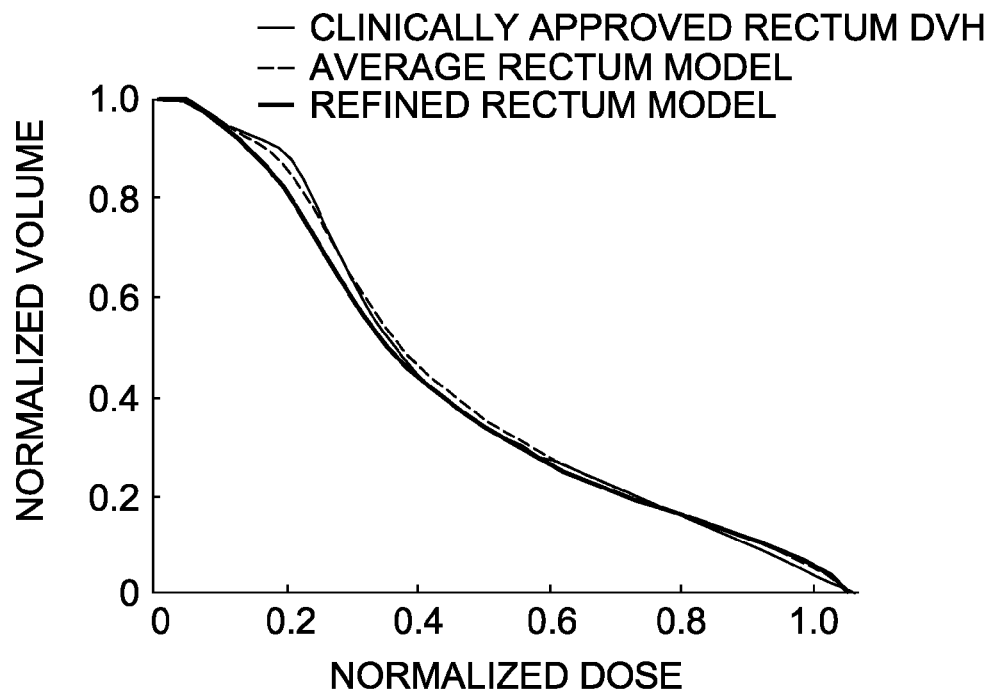
Figure 15D:
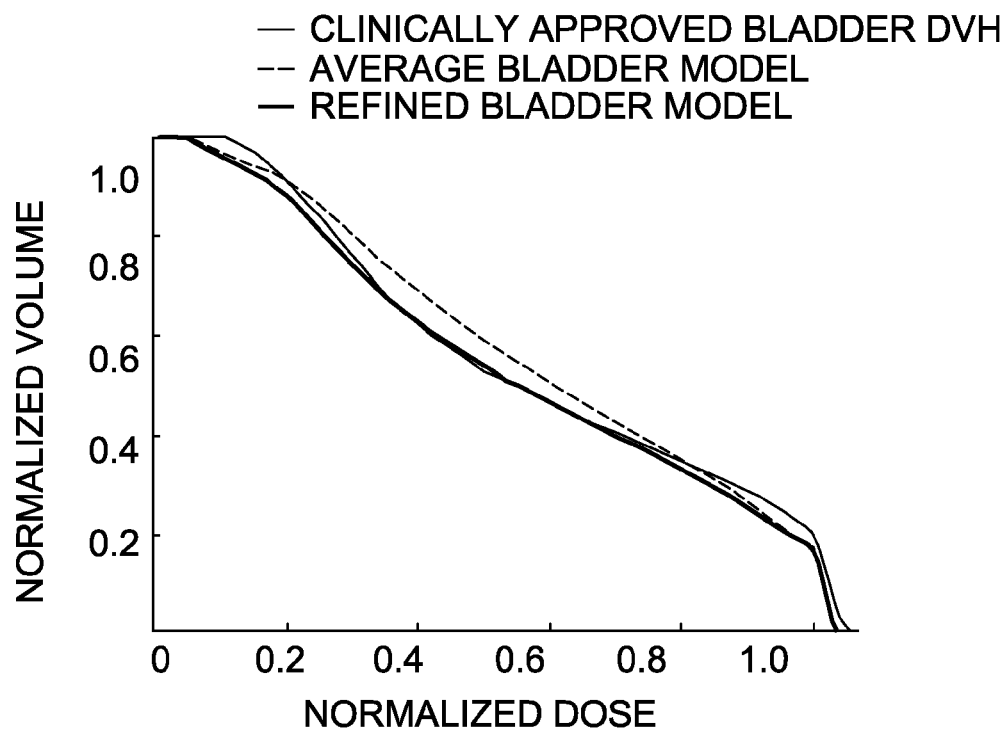
Figure 15E:
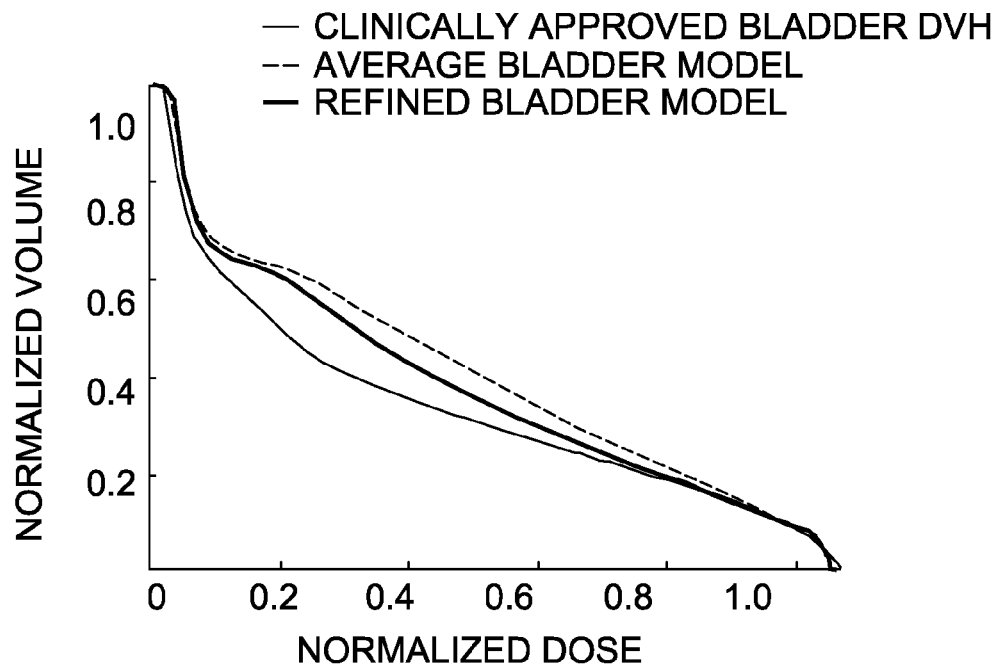
Figure 15F:
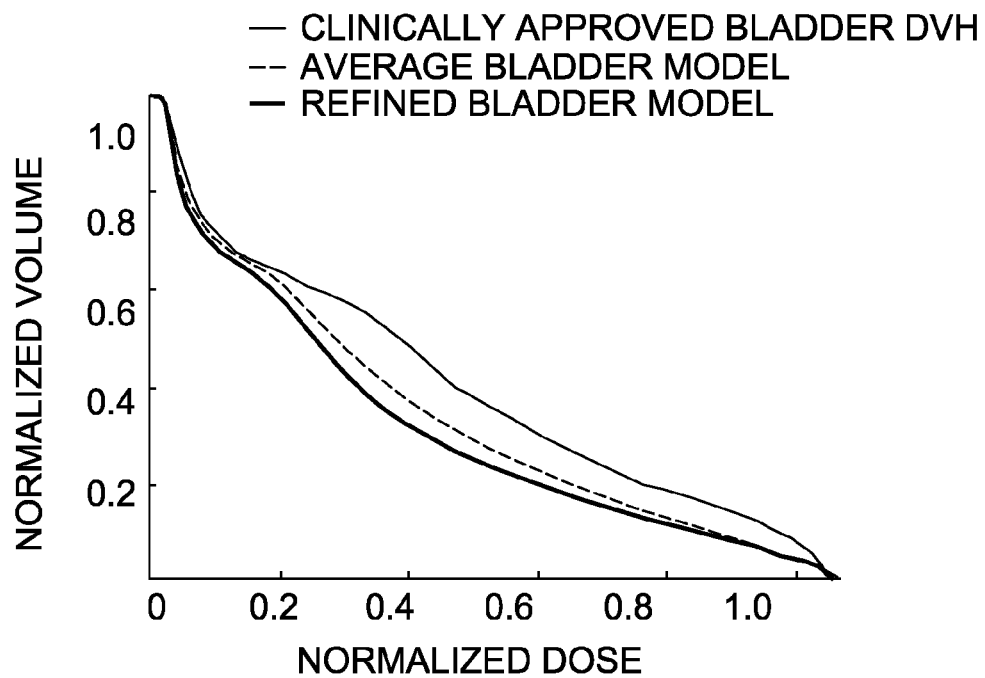
Figure 16A:
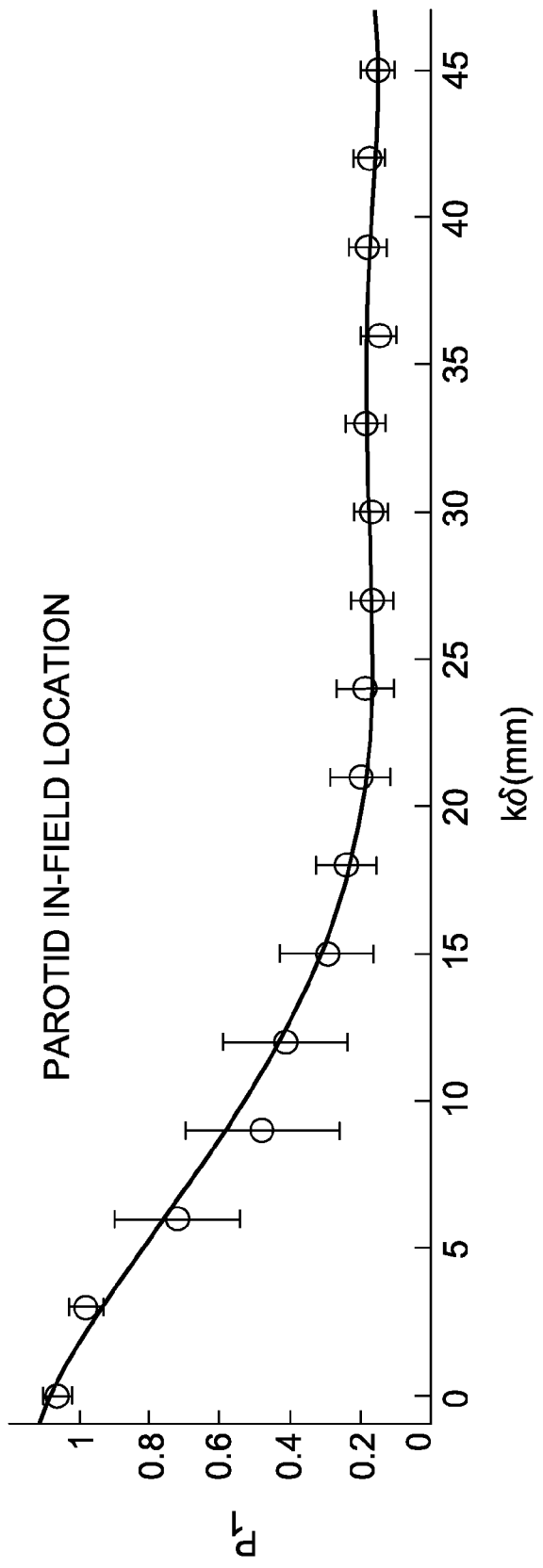
FIGS. 16A-16F are graphs depicting parotid in-field and out-of-field parameter trajectories.
Figure 16B:
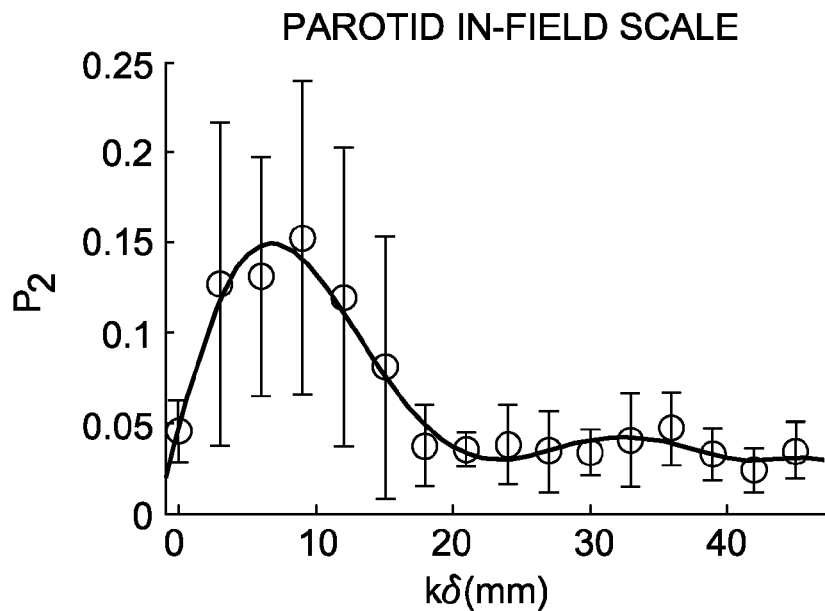
Figure 16C:
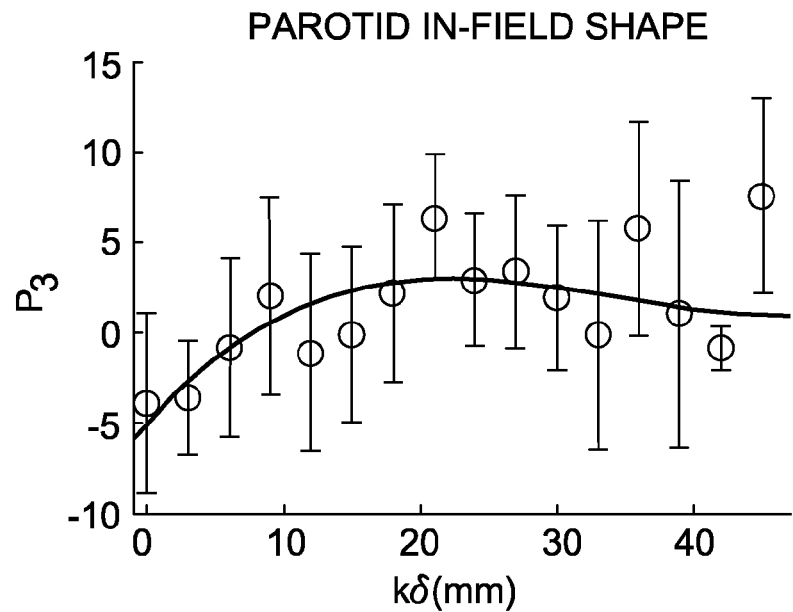
Figure 16D:
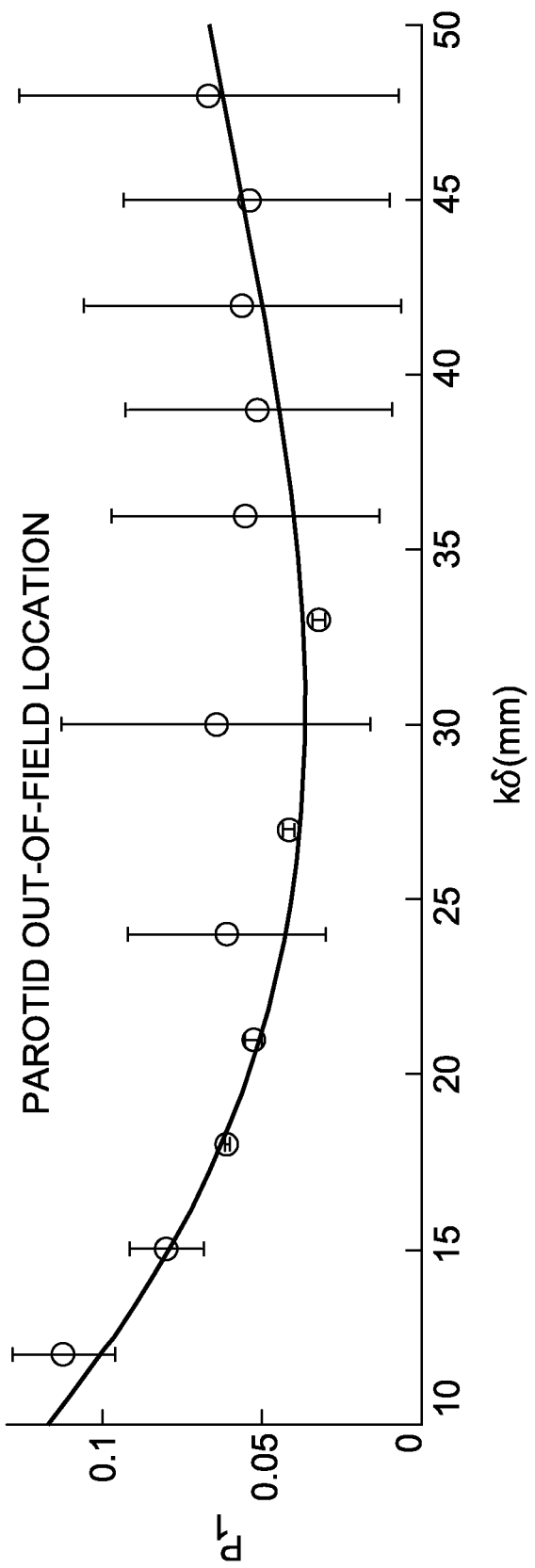
Figure 16E:
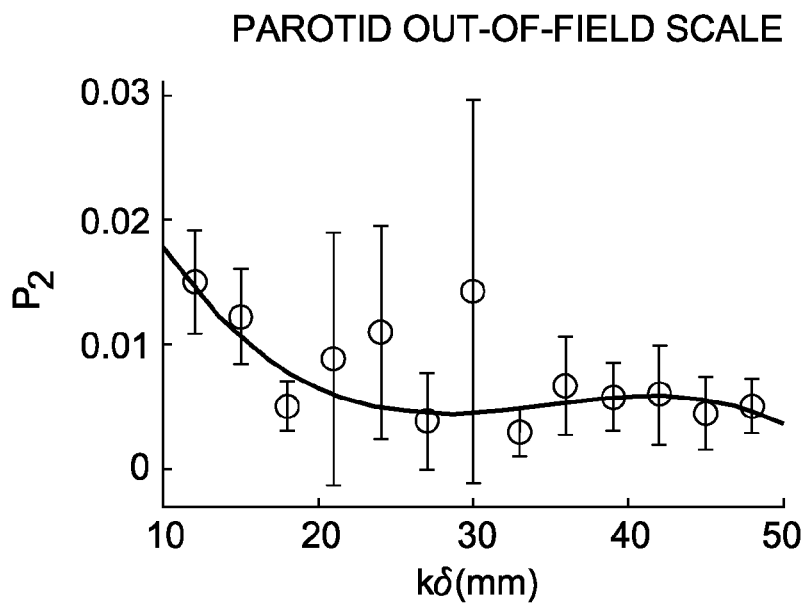
Figure 16F:
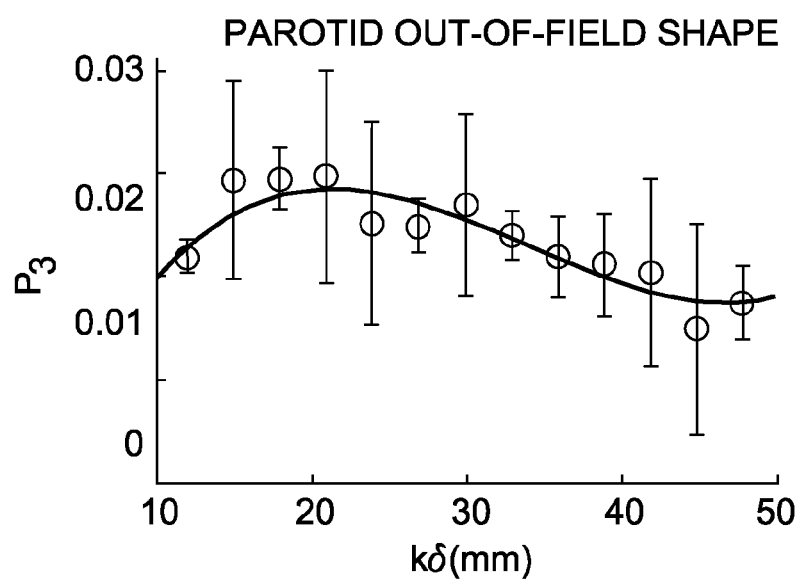

FIGS. 13A and 13B show the strong correlation between predicted gains (RSR, Equation 15) and actualized gains ($SR_{orig}-SR_{replan}$, Equation 13) for the bladder and rectum, respectively. These data also demonstrate the low rate of false positives (minimal population in the lower right portion of the graph) and false negatives (minimal population in the upper left portion of the graph).

Repeating this process for the parotid gland OAR in head-and-neck IMRT, 24 clinically-approved treatment plans were used as a training cohort to develop an AVERAGE model. FIGS. 16A-16F show the parameter trajectories for the in-field and out-of-field portions of the parotid model.

Figure 12A:
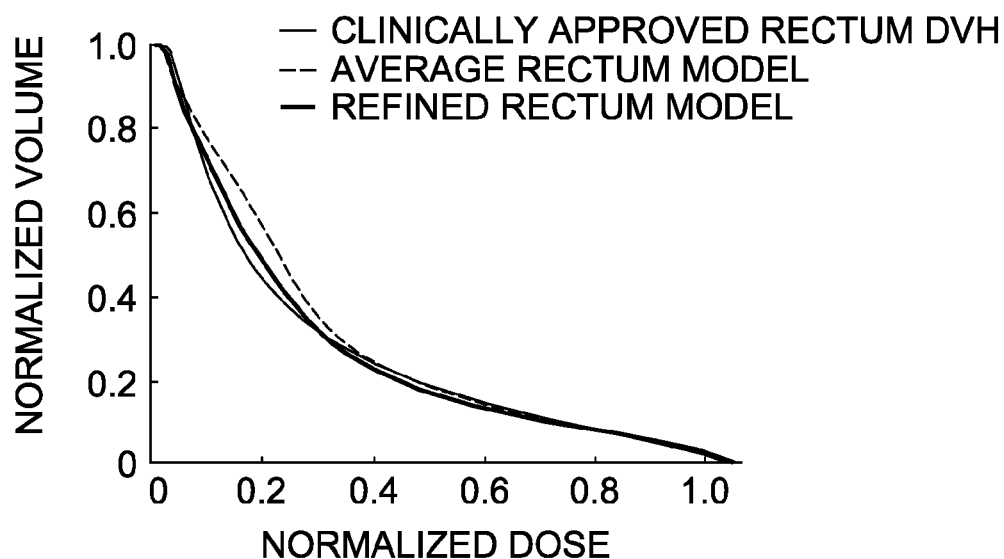
FIGS. 12A-12F are graphs demonstrating the concordance of two predictive DVH models to the clinically-approved rectum and bladder DVHs from the training set.
Figure 12B:
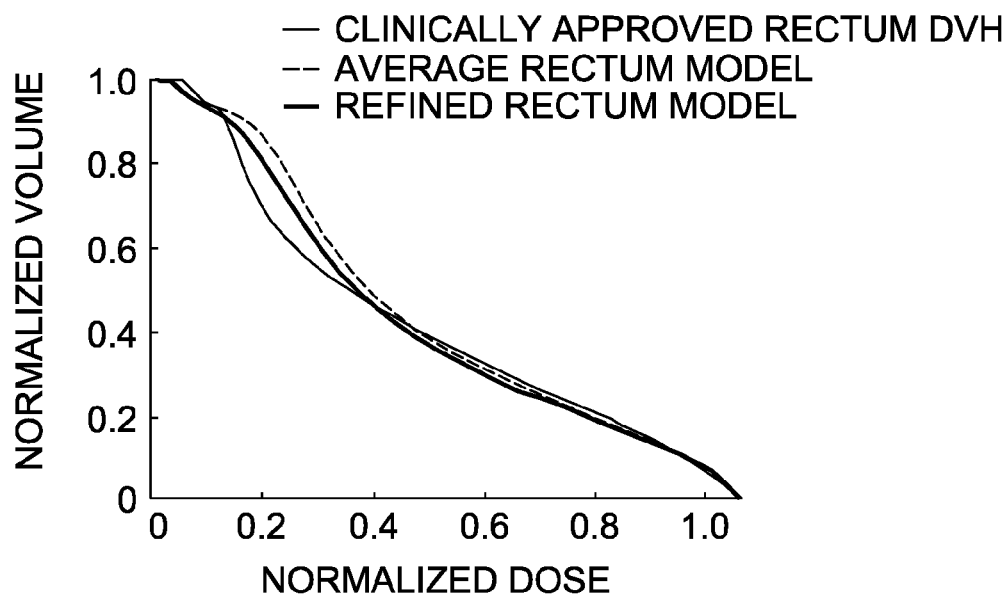
Figure 12C:
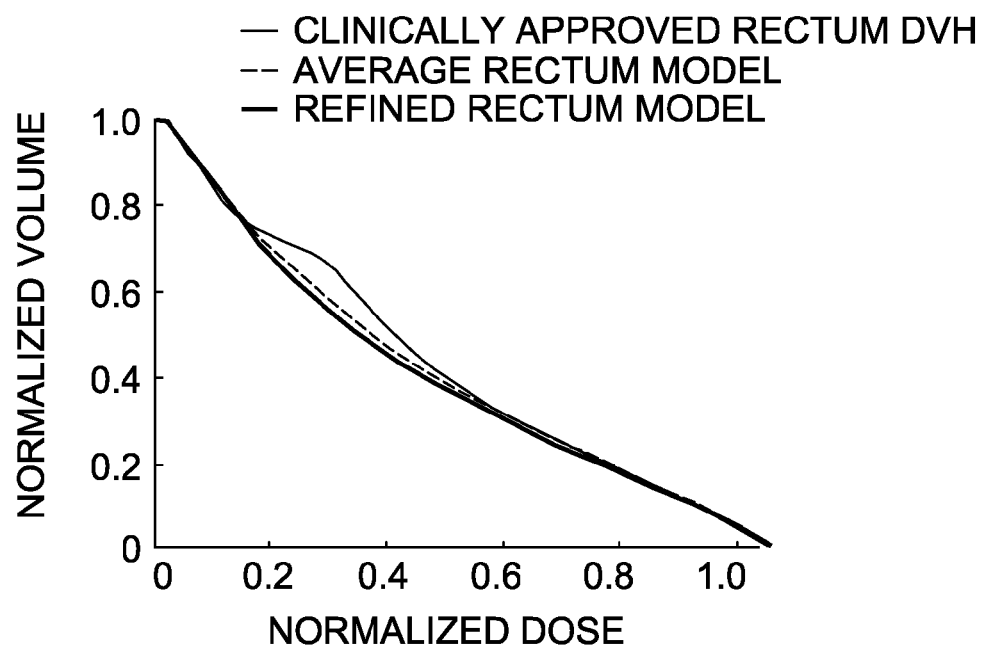
Figure 12D:
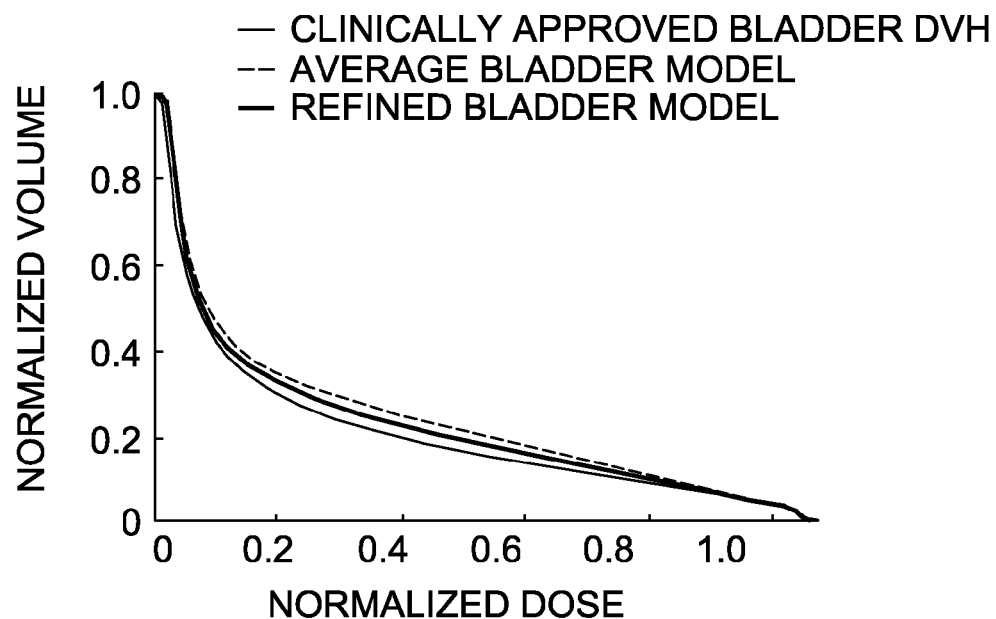
Figure 12E:
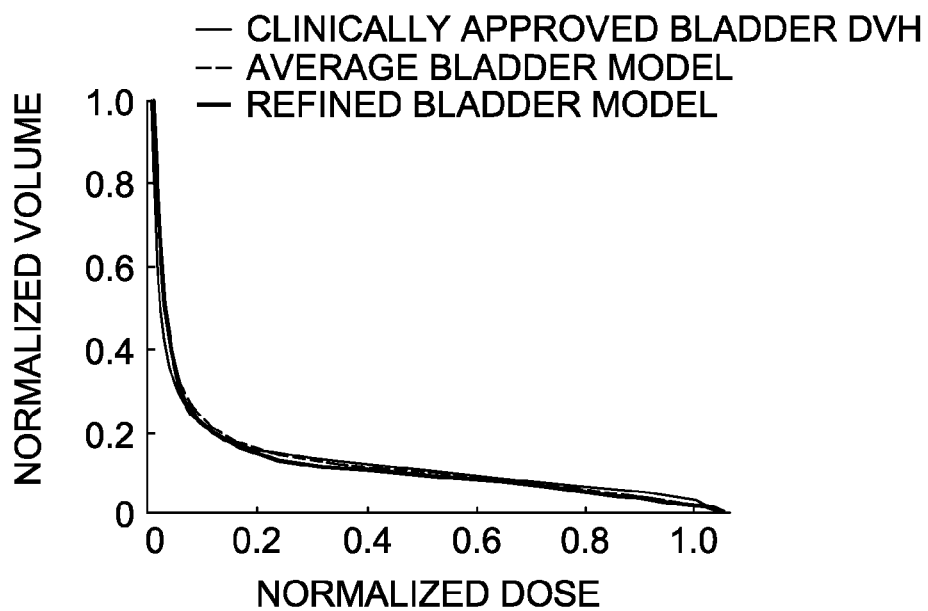
Figure 12F:
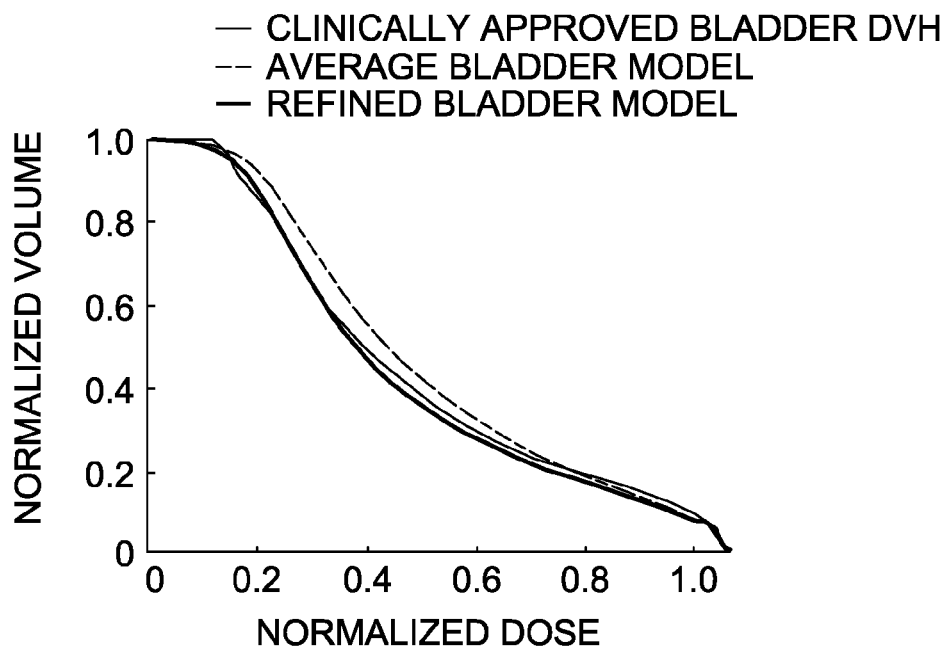
Figure 17A:
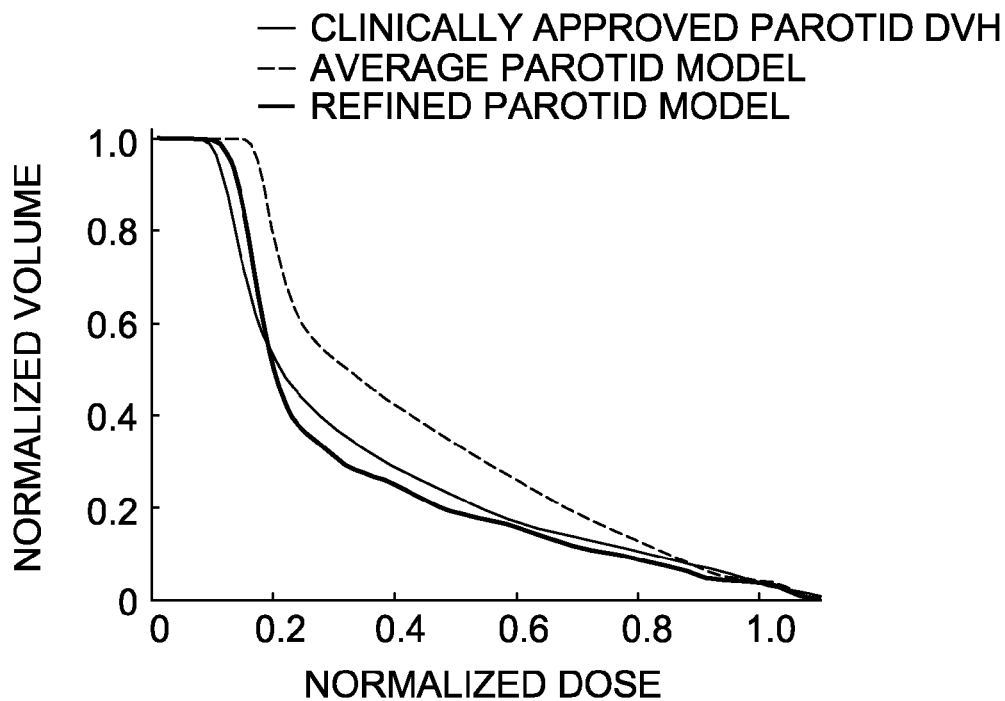
FIGS. 17A-17F are graphs demonstrating the concordance of two predictive DVH models to clinically-approved parotid DVHs from the training set.
Figure 17B:
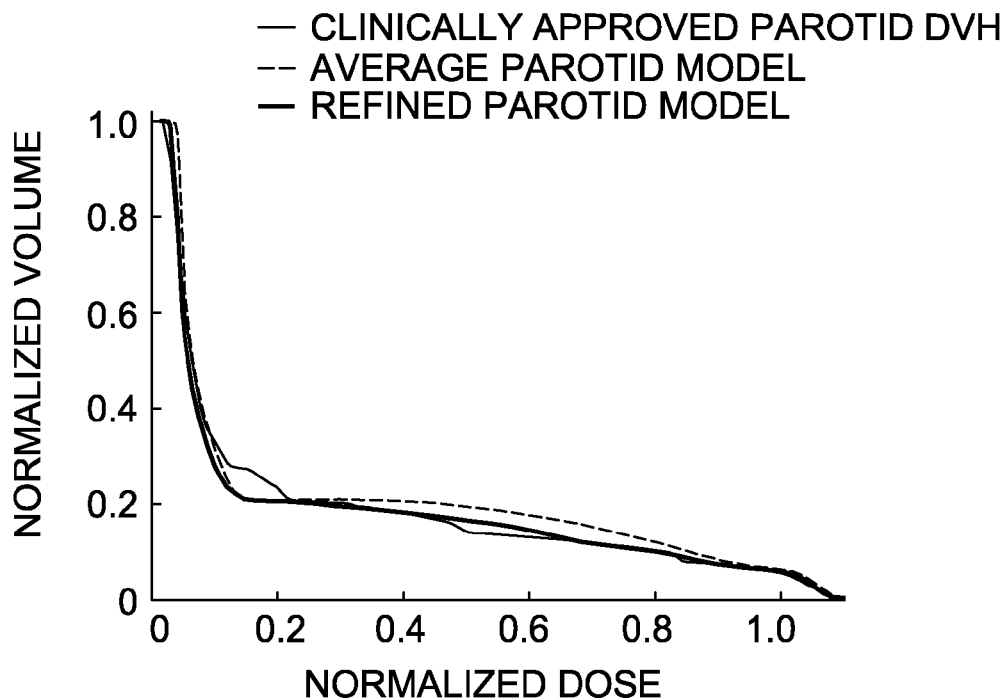
Figure 17C:
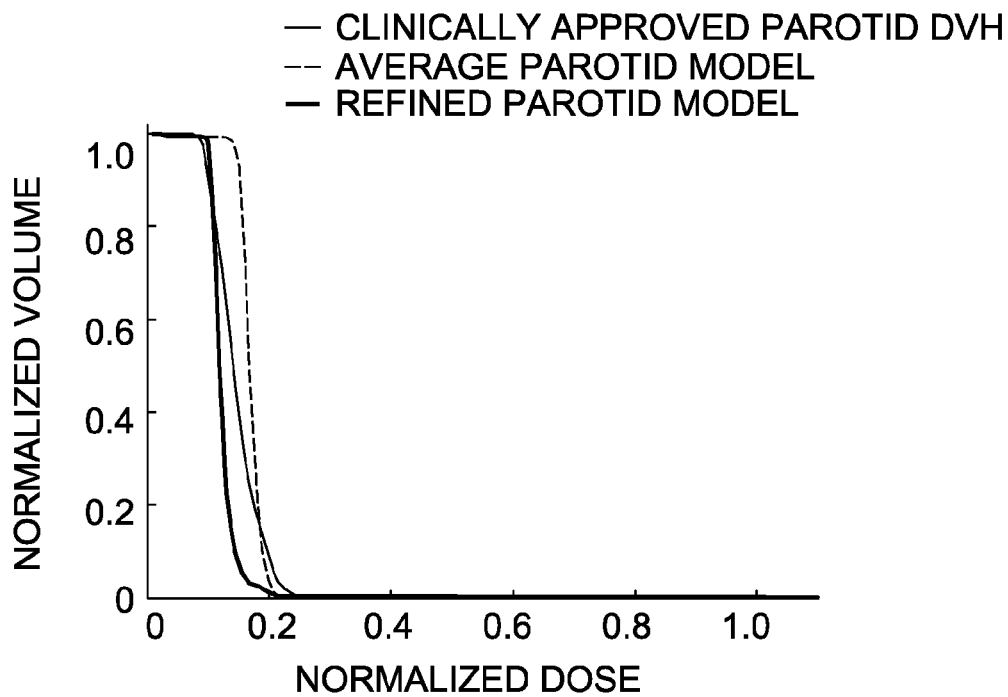
Figure 17D:
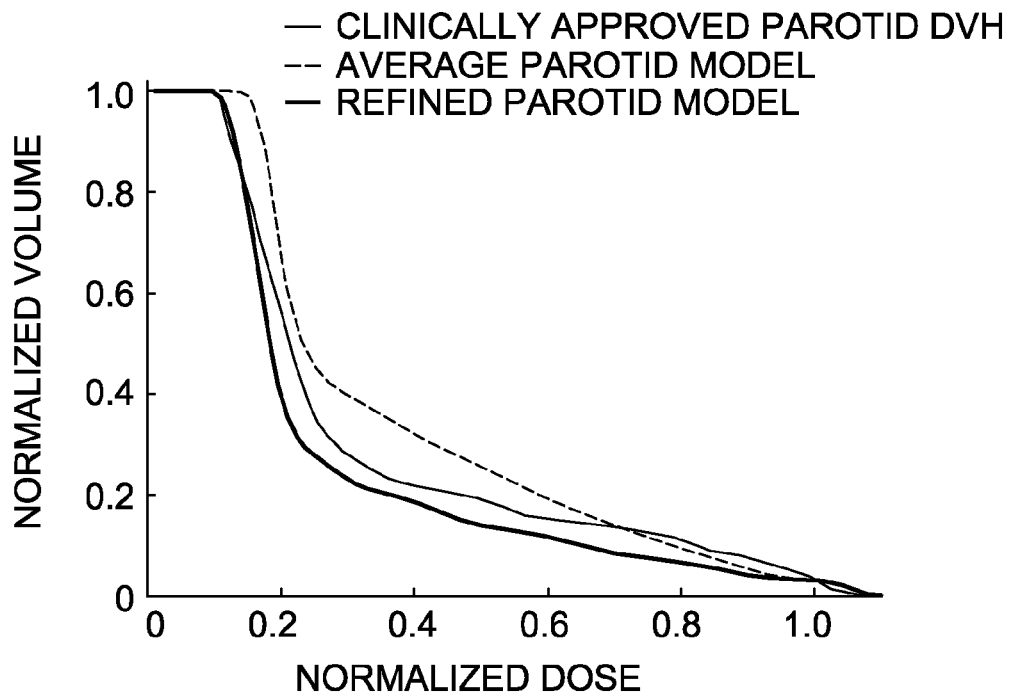
Figure 17E:
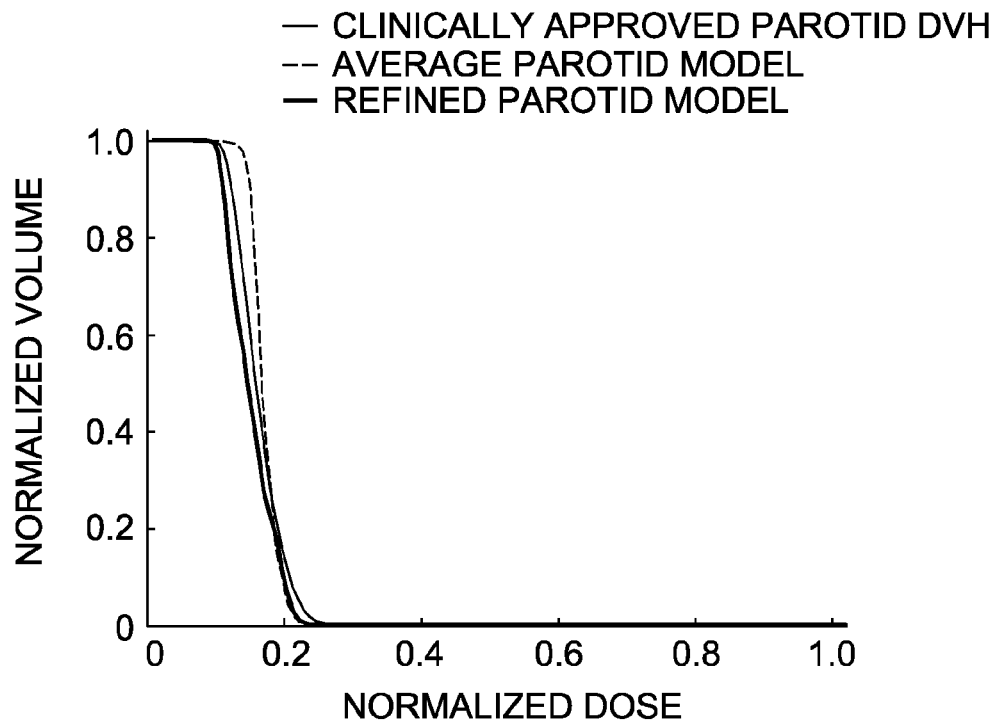
Figure 17F:
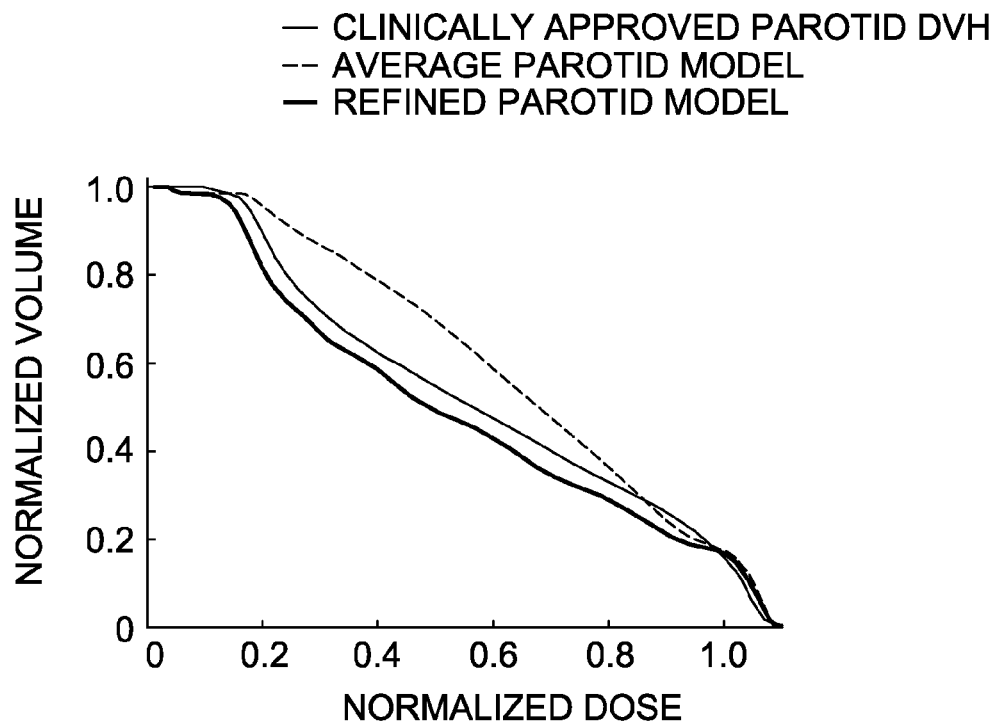

Because of the small initial sample size, the model validation step was omitted and only the second validation procedure (FIG. 10B) was conducted. Five patients were identified as potentially sub-optimal and removed from the training cohort to develop the REFINED model. FIGS. 17A-12F demonstrates both AVERAGE and REFINED models' DVH predictions against six clinically-approved plans for the parotid. Both demonstrated good concordance with the REFINED model more closely matching the observed DVHs.

Figure 18A:
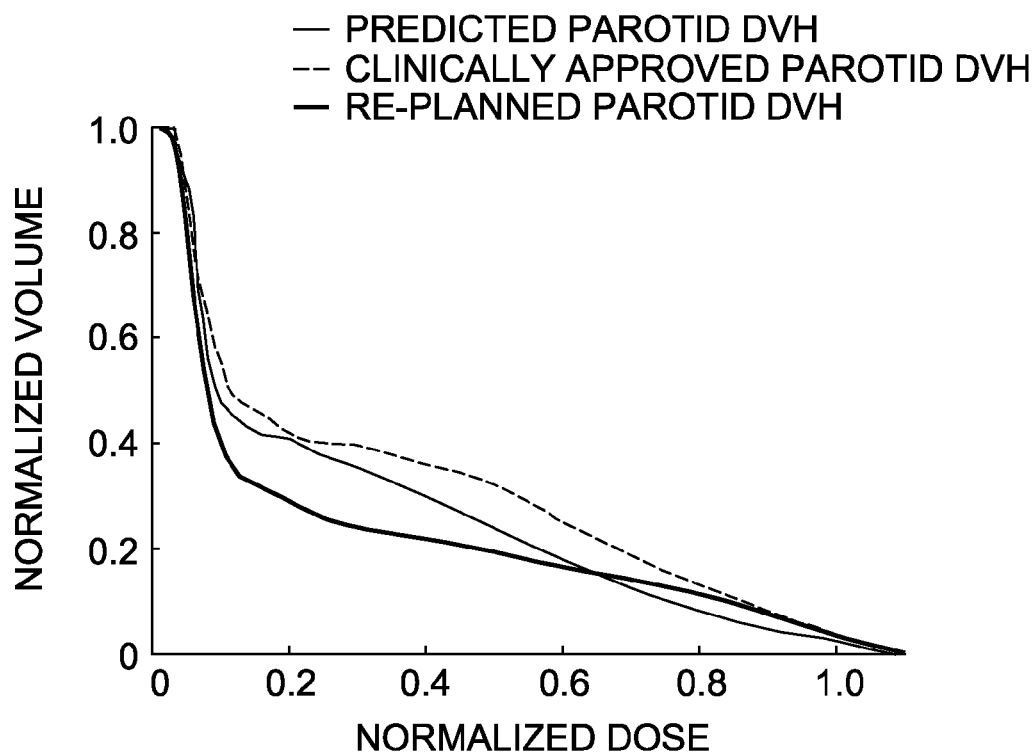
FIGS. 18A-18C are graphs depicting predicted parotid DVHs correctly identifying plans that could be improved under re-planning.
Figure 18B:
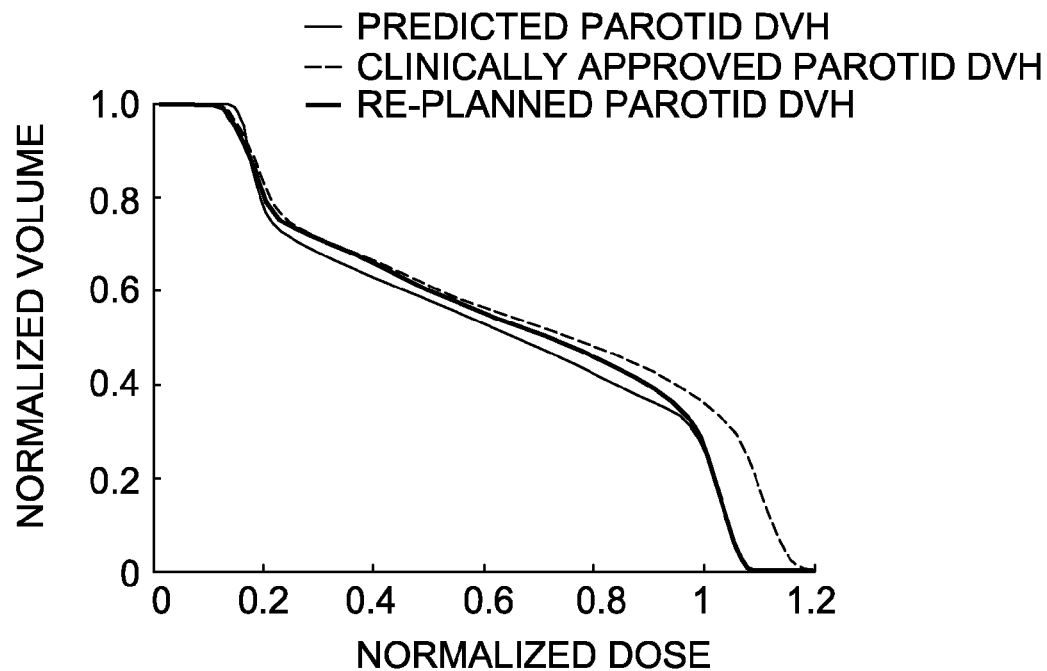
Figure 18C:
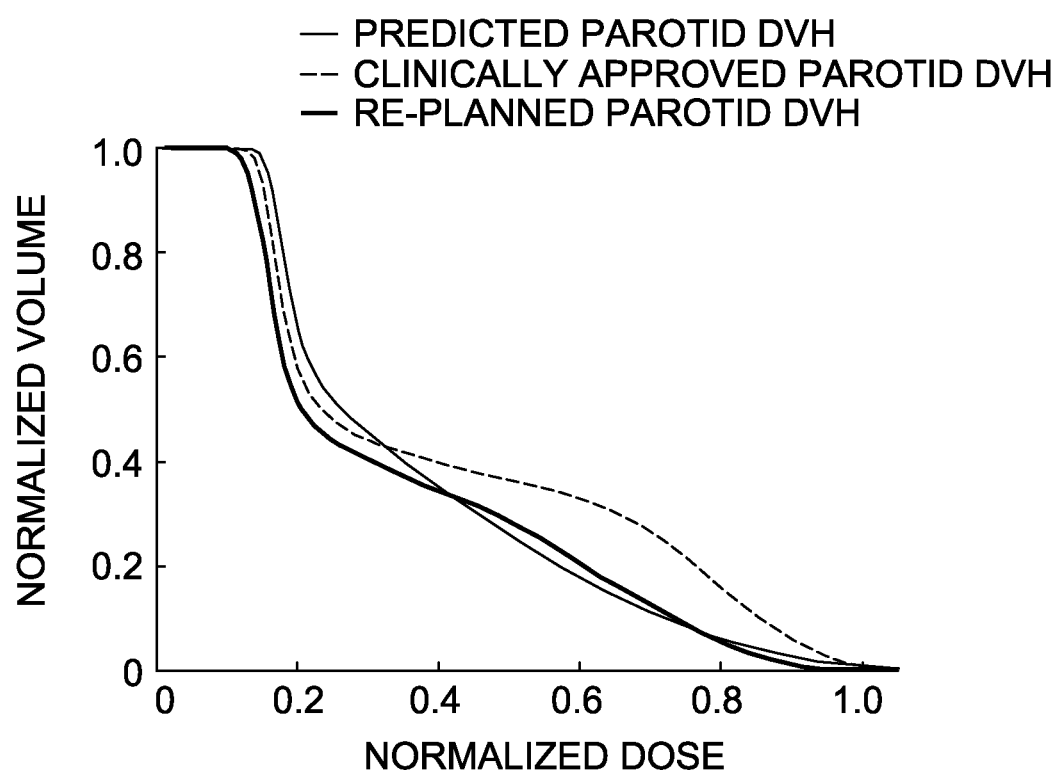

FIGS. 18A-18C show the identification of sub-optimal plans in the training cohort by the AVERAGE model and the demonstration through re-planning of the realized improvements.

Figure 19:
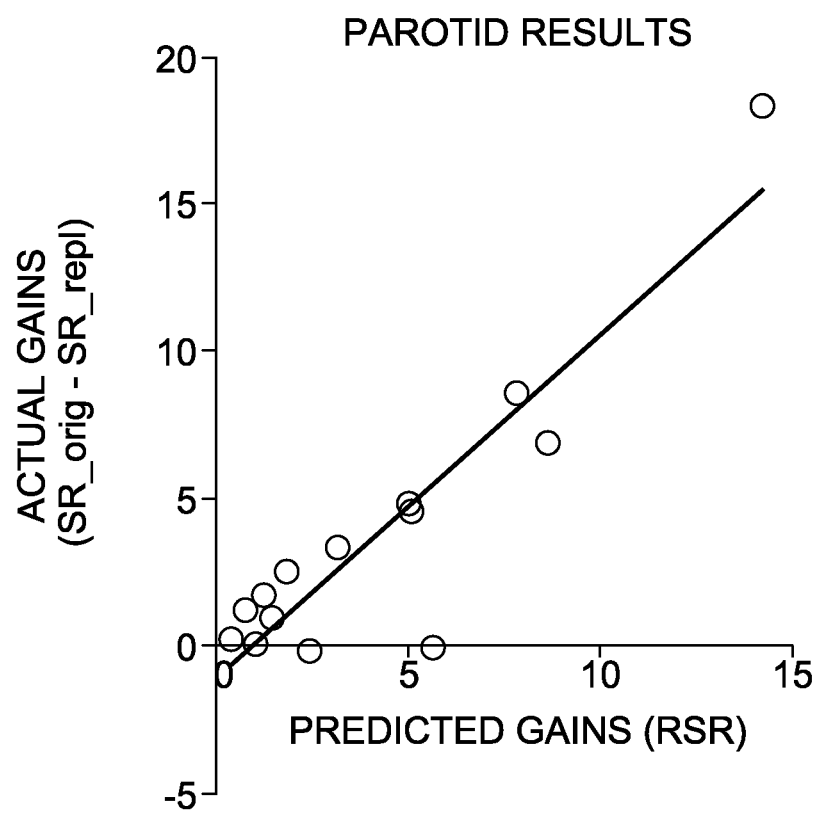
FIG. 19 demonstrates the correlation between predicted gains and gains realized through re-planning, validating the parotid model's ability to correctly distinguish optimal and sub-optimal treatment plans.

FIG. 19 shows the strong correlation between predicted gains (RSR, Equation 15) and actualized gains ($SR_{orig}-SR_{replan}$, Equation 13). These data also demonstrate the low rate of false positives (minimal population in the lower right portion of the graph) and false negatives (minimal population in the upper left portion of the graph).

The SR and RSR formalism for comparing DVHs is but one method of comparison most appropriate for parallel-functioning organs such as the parotids or the liver. It is known that in serial organs like the rectum or the spinal cord the high dose portion of the DVH is most correlated to radiation-induced complications. It is possible to consider instead specific DVH point differences. e.g., $\epsilon$ (40 Gy) or $\epsilon$ (65 Gy), though this would ignore all other parts of the DVH curves. One modification of the DVH comparison could immediately convert into an existing radiobiological formalism via the generalized restricted sum of residuals (gRSR), as shown in Equation 17 below $$gRSR_{ij} = \sum_{D=0}^{\infty} \varepsilon_{ij}^{+}(D) \cdot D^{a-1} \tag{17}$$

where a is the order parameter in the introduction of generalized equivalent uniform dose (gEUD). In a one-to-one correspondence to the gEUD concept, a=1 for parallel organs and gRSR reverts to the simple restricted sum of residuals. For serial OARs, the value of a will be greater than unity, meaning the higher dose deviations will receive higher weighting as compared to the lower dose differences. Current understanding of organ response can be immediately brought to bear when developing predictive dose-volume models for specific organs.

The embodiments illustrated and described herein as well as embodiments not specifically described herein but within the scope of aspects of the invention constitute exemplary means for correlating a dose-volume relationship (e.g., mean dose, dose-volume histogram, equivalent uniform dose, 3-D dose distribution) to boundary distance vectors from the voxels of one or more OAR to a boundary of a PTV.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention of the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A radiation system for developing a predictive dose-volume relationship for a radiation therapy treatment, the system comprising:
    a radiation data memory device for storing data corresponding to a plurality of patients, the data comprising a three-dimensional representation of a planning target volume and one or more organs-at-risk, the data further comprising an amount of radiation delivered to the planning target volume and the one or more organs-at-risk;
    a display device; and
    one or more radiation data processors programmed to:
        access, from the radiation data memory device, the data corresponding to the plurality of patients;
        develop a model that predicts dose-volume relationships using the three-dimensional representations of the planning target volume and the one or more organs-at-risk from the data corresponding to the plurality of patients, wherein the model is developed by:
            calculating a dose-volume relationship corresponding to the irradiation of the planning target volume for each patient of the plurality of patients;
            calculating a set of minimum distance vectors between discrete volume elements of the one or more organs-at-risk and a boundary surface of the planning target volume; and
            determining a correlation between the calculated dose-volume relationship and the calculated set of minimum distance vectors between the one or more organs-at-risk to the boundary surface of the planning target volume using a probability distribution function to fit the set of minimum distance vectors;
        receive data corresponding to a three-dimensional representation of the planning target volume and the one or more organs-at-risk of a new patient;
        calculate minimum distance vectors between discrete volume elements of the one or more organs-at-risk of the new patient and a boundary surface of the planning target volume of the new patient;
        predict dose-volume relationships for the planning target volume and the one or more organs-at-risk of the new patient using the developed model and the calculated minimum distance vectors for the new patient; and
        treat the new patient based at least in part on the predicted dose-volume relationships for the planning target volume and the one or more organs-at-risk of the new patient.

2. The radiation system of claim 1, wherein the planning target volume comprises a portion of a patient's body desired to receive radiation.

3. The radiation system of claim 1, wherein the radiation data processor is further programmed to optimize the model that predicts dose-volume relationships, wherein optimizing the model that predicts dose-volume relationships comprises:
    comparing the model to each of the calculated dose-volume relationships;
    determining which of the calculated dose-volume relationships are optimal based on the comparing; and
    determining a correlation between the optimal dose-volume relationships and the calculated set of minimum distance vectors between discrete volume elements of the one or more organs-at-risk and the boundary surface of the planning target volume.

4. The radiation system of claim 1, further comprising a display device configured to present the predictive dose-volume relationships for irradiating the planning target volume to a user.

5. The radiation system of claim 1, further comprising a means for correlating a dose-volume relationship to the boundary distance vectors from voxels of the one or more organs-at-risk to the planning target volume.

6. The radiation system of claim 1, wherein the one or more radiation data processors are further programmed to determine, based on the model, predictive dose-volume relationships for a radiation therapy treatment based only on the three-dimensional representation of the planning target volume and one or more organs-at-risk.

7. The radiation system of claim 1, wherein the planning target volume comprises a tumor.

8. The radiation system of claim 1, wherein the one or more radiation data processors are further programmed to determine the correlation between the calculated dose-volume relationship and the calculated set of minimum distance vectors between the one or more organs-at-risk to the boundary surface of the planning target volume by fitting an evolution of at least one parameter of the probability distribution function as a function of the calculated minimum distance vectors.

9. A method comprising:
    receiving, by a radiation system, data corresponding to a radiation of a planning target volume in a plurality of patients, the data comprising a three-dimensional representation of the planning target volume and one or more organs-at-risk, the data further comprising an amount of radiation delivered to the planning target volume and the one or more organs-at-risk;
    developing, by the radiation system, a model that predicts dose-volume relationships using the three-dimensional representations of the planning target volume and the one or more organs-at-risk from the received data, wherein developing the model comprises:
        calculating a dose-volume relationship corresponding to the irradiation of the planning target volume for each patient of the plurality of patients;
        calculating a set of minimum distance vectors between discrete volume elements of the one or more organs-at-risk and a boundary surface of the planning target volume; and
        determining a correlation between the calculated dose-volume relationship and the calculated set of minimum distance vectors between the one or more organs-at-risk to the boundary surface of the planning target volume using a probability distribution function to fit the set of minimum distance vectors;

receiving, by the radiation system, data corresponding to a three-dimensional representation of the planning target volume and one or more organs-at-risk of a new patient;

calculating, by the radiation system, minimum distance vectors between discrete volume elements of the one or more organs-at-risk of the new patient and a boundary surface of the planning target volume of the new patient;

predicting dose-volume relationships for the planning target volume and the one or more organs-at-risk of the new patient using the developed model and the calculated minimum distance vectors for the new patient; and treating the new patient based at least in part on the predicted dose-volume relationships for the planning target volume and the one or more organs-at-risk of the new patient.

10. The method of claim 9, wherein the planning target volume comprises a tumor and any additional volume to be irradiated.

11. The method of claim 9, wherein the predictive dose-volume relationship correlates a dose-volume relationship to boundary distance vectors from voxels of the one or more organs-at-risk to the surface of the planning target volume.

12. The method of claim 9, further comprising optimizing the model that predicts dose-volume relationships.

13. The method of claim 12, wherein optimizing the model that predicts dose-volume relationships comprises:
comparing the model to each of the calculated dose-volume relationships;
determining which of the calculated dose-volume relationships are optimal based on the comparing; and
determining a correlation between the optimal dose-volume relationships and the set of minimum boundary distance vectors from the one or more organs-at-risk to the surface of the planning target volume.

14. One or more non-transitory computer storage media embodying computer-executable components, said components comprising:
an interface component that when executed by at least one radiation data processor in a radiation system causes the at least one radiation data processor to receive data corresponding to a radiation of a planning target volume in a plurality of patients, the data comprising a three-dimensional representation of the planning target volume and one or more organs-at-risk, the data further comprising an amount of radiation delivered to the planning target volume and the one or more organs-at-risk;
a correlation component that when executed by the at least one radiation data processor in the radiation system causes the at least one radiation data processor to develop a model that predicts dose-volume relationships using the three-dimensional representations of the planning target volume and the one or more organs-at-risk from the received data, by:
calculating a dose-volume relationship corresponding to the irradiation of the planning target volume for each patient of the plurality of patients;
calculating a set of minimum distance vectors between discrete volume elements of the one or more organs-at-risk and a boundary surface of the planning target volume; and
determining a correlation between the calculated dose-volume relationship and the calculated set of minimum distance vectors between the one or more organs-at-risk to the boundary surface of the planning target volume using a probability distribution function to fit the set of minimum distance vectors;
an component that when executed by the at least one radiation data processor in the radiation system causes the at least one radiation data processor to receive data corresponding to a three-dimensional representation of the planning target volume and the one or more organs-at-risk of a new patient;
an component that when executed by the at least one radiation data processor in the radiation system causes the at least one radiation data processor to calculate minimum distance vectors between discrete volume elements of the one or more organs-at-risk of the new patient and a boundary surface of the planning target volume of the new patient;
a component that when executed by the at least one radiation data processor in the radiation system causes the at least one radiation data processor to predict dose-volume relationships for the planning target volume and the one or more organs-at-risk of the new patient using the developed model and the calculated minimum distance vectors for the new patient; and
a component that when executed by the at least one radiation data processor in the radiation system treats the new patient based at least in part on the predicted dose-volume relationships for the planning target volume and the one or more organs-at-risk of the new patient.

15. The non-transitory computer storage media of claim 14, wherein execution of the correlation component by the at least one radiation data processor further comprises optimizing the model that predicts dose-volume relationships.

16. The non-transitory computer storage media of claim 15, wherein execution of the correlation component by the at least one radiation data processor to optimize the model that predicts dose-volume relationships comprises:
comparing the model to each of the calculated dose-volume relationships;
determining which of the calculated dose-volume relationships are optimal based on the comparing; and
determining a correlation between the optimal dose-volume relationships and the minimum boundary distance vectors from the one or more organs-at-risk to the surface of the planning target volume.

17. The non-transitory computer storage media of claim 14, further comprising a display component that when executed by at least one radiation data processor causes the at least one radiation data processor to present the predictive dose-volume relationships for a radiation therapy treatment to a user.

18. The non-transitory computer storage media of claim 14, wherein the planning target volume comprises a tumor.

* * * * *